(12) United States Patent
Wszola et al.

(10) Patent No.: US 12,208,179 B2
(45) Date of Patent: Jan. 28, 2025

(54) DETERGENT-FREE DECELLULARIZED EXTRACELLULAR MATRIX PREPARATION METHODS AND BIOINKS FOR 3D PRINTING

(71) Applicant: Polbionica Sp. z o. o., Warsaw (PL)

(72) Inventors: Michal Wszola, Warsaw (PL); Marta Klak, Pila (PL); Andrzej Berman, Warsaw (PL); Katarzyna Kosowska, Jastrzab (PL); Tomasz Bryniarski, Nowy Targ (PL); Tomasz Dobrzanski, Warsaw (PL); Grzegorz Tymicki, Lopiennik Gorny (PL); Magdalena Gomólka, Ostrow Wielkopolski (PL); Patrycja Kowalska, Warsaw (PL); Piotr Cywoniuk, Plock (PL); Paweł Turowski, Warsaw (PL); Igor Zamora, Fugasowka (PL); Ewa Olender, Warsaw (PL); Radoslaw Olkowski, Warsaw (PL); Artur Kamiński, Warsaw (PL)

(73) Assignee: Polbionica Sp. z o. o., Warsaw (PL)

( * ) Notice: Subject to any disclaimer, the term of this patent is extended or adjusted under 35 U.S.C. 154(b) by 579 days.

(21) Appl. No.: 17/628,429

(22) PCT Filed: Jul. 21, 2020

(86) PCT No.: PCT/IB2020/056856
§ 371 (c)(1),
(2) Date: Jan. 19, 2022

(87) PCT Pub. No.: WO2021/014359
PCT Pub. Date: Jan. 28, 2021

(65) Prior Publication Data
US 2022/0280694 A1  Sep. 8, 2022

(30) Foreign Application Priority Data

Jul. 22, 2019 (EP) .................................... 19461559
Dec. 19, 2019 (EP) .................................... 19218191

(51) Int. Cl.
| | |
|---|---|
| *A61L 27/36* | (2006.01) |
| *B33Y 10/00* | (2015.01) |
| *B33Y 40/20* | (2020.01) |
| *B33Y 70/00* | (2020.01) |
| *C09D 4/06* | (2006.01) |
| *C09D 7/63* | (2018.01) |
| *C09D 7/65* | (2018.01) |
| *C09D 133/14* | (2006.01) |

(52) U.S. Cl.
CPC ....... *A61L 27/3687* (2013.01); *A61L 27/3691* (2013.01); *B33Y 10/00* (2014.12); *B33Y 40/20* (2020.01); *B33Y 70/00* (2014.12); *C09D 4/06* (2013.01); *C09D 7/63* (2018.01); *C09D 7/65* (2018.01); *C09D 133/14* (2013.01)

(58) Field of Classification Search
CPC ............. A61L 27/3687; A61L 27/3691; A61L 27/3808; A61L 2300/414; A61L 2300/426; A61L 2300/428; A61L 27/26; A61L 27/3633; A61L 27/3683; A61L 27/54; A61L 27/507; B33Y 10/00; B33Y 40/20; B33Y 70/00; B33Y 80/00; C09D 4/06; C09D 7/63; C09D 7/65; C09D 133/14; C08L 5/08; C08L 89/06; C08L 1/26
See application file for complete search history.

(56) References Cited

U.S. PATENT DOCUMENTS

2016/0279170 A1  9/2016  Katane et al.

FOREIGN PATENT DOCUMENTS

| KR | 101628821 B1 | 6/2016 |
| KR | 20180011607 A | 2/2018 |
| KR | 20180125776 A | 11/2018 |
| WO | 2016126947 A2 | 8/2016 |
| WO | 2017014582 A1 | 1/2017 |

OTHER PUBLICATIONS

Ali et al., "A Photo-crosslinkable Kidney ECM-derived Bioink Accelerates Renal Tissue Formation" Adv Healthc Mater: Apr. 2019; 8(7): e1800992. doi:10.1002/adhm.201800992, available in PMC Feb. 24, 2020, 23 pages.
Brown et al., "Comparison of Three Methods for the Derivation of a Biologic Scaffold Composed of Adipose Tissue Extracellular Matrix" Tissue Engineering: Part C, vol. 17, No. 4, DOI: 10.1089/ten.tec.2010.0342, 2011, 14 pages.
Chen et al., "Desktop-sterolithography 3D printing of a radially oriented extracellular matrix/mesenchymal stem cell exosome bioink for osteochondral defect regeneration" Theranostics 2019, vol. 9, Issue 9, doi: 10.7150/thno.31017, Ivyspring International Publisher, Published Apr. 13, 2019, 21 pages.

(Continued)

*Primary Examiner* — Mina Haghighatian
*Assistant Examiner* — Nathan W Schlientz
(74) *Attorney, Agent, or Firm* — Ziegler IP Law Group LLC.

(57) ABSTRACT

A detergent-free decellularized ECM preparation method, a detergent-free decellularized ECM in a powder form and in a liquid form, a method of preparation of a primary bioink, the primary bioink, a method of preparation of a vascular bioink, the vascular bioink, a three dimensional structure including the primary bioink and/or the vascular bioink and a method of preparation of the three-dimensional structure.

13 Claims, 10 Drawing Sheets

(56) References Cited

OTHER PUBLICATIONS

Chimene et al., "Advanced Bioinks for 3D Printing: A Materials Science Perspective" Annals of Biomedical Engineering, Springer US, New York, vol. 44, No. 6, May 16, 2016, ISSN: 0090-6964, Doi: 10.1007/S10439-016-1638-Y, 13 pages.
International Search Report, European Patent Office, Application No. PCT/IB2020/056856, mailed Oct. 23, 2020, 3 pages.
Lee et al., "Development of liver decellularized extracellular matrix bioink for 3D cell printing-based liver tissue engineering" Biomacromolecules, Just Accepted Manuscript, ACS Publications, DOI: 10.1021/acs.biomac . . . 6b01908, Published Mar. 9, 2017, 29 pages.
Mirmalek-Sani et al., "Porcine pancreas extracellular matrix as a platform for endocrine pancreas bioengineering" Biomaterials (2013), http://dx.doi.org/10.1016/j.biomaterials.2013.03.054, Accepted Mar. 15, 2013, 8 pages.
Pati et al., "Printing three-dimensional tissue analogues with decellularized extracellular matrix bioink" Nature Communications, DOI:10.1038/ncomms4935, Macmillan Publishers Limited, Published Jun. 2, 2014, 11 pages.
Sackett et al., "Extracellular matrix scaffold and hydrogel derived from decellularized and delipidized human pancreas" Scientific Reports (2018), DOI: 10.1038/s41598-28857-1, www.nature.com/scientificreports, Published online Jul. 11, 2018, 16 pages.
Skardal et al., "Photocrosslinkable hyaluronan-Gelatin Hydrogels for Two-Step Bioprinting" Tissue Engineering: Part A, vol. 16, No. 8, Aug. 1, 2010, ISSN: 1937-3341, DOI: 10.1089/ten.tea.2009.0798, 12 pages.
European Patent Office, Communication under Rule 71(3), Application No. 20 757 665.3-1109, Dated Mar. 7, 2024, 8 Pages.
European Patent Office, Decision to grant a European patent pursuant to Article 97(1) EPC, Application No. 20757665.3-1109 / 4003493, Dated May 25, 2024, 2 Pages.
European Patent Office, Intention to grant a European patent, Application No. EP20757665, Dated Mar. 7, 2024, 103 Pages.
International Bureau of WIPO, International Preliminary Report on Patentability, International Application No. PCT/IB2020/056856, Filing Date Jul. 21, 2020, 9 Pages.
European Patent Office, Text Intended for Grant, Decision to grant a European patent pursuant to Article 97(1) EPC, Application No. 20757665.3-1109 / 4003493, Dated May 25, 2024, 52 Pages.

DETERGENT-FREE DECELLULARIZED EXTRACELLULAR MATRIX PREPARATION METHODS AND BIOINKS FOR 3D PRINTING

FIELD

The aspects of the disclosed embodiments concern a detergent-free decellularized ECM preparation method, a detergent-free decellularized ECM in a powder form and in a liquid form, a method of preparation of a primary bioink, the primary bioink, a method of preparation of a vascular bioink, the vascular bioink, a three dimensional structure comprising the primary bioink and/or the vascular bioink and a method of preparation of the three-dimensional structure.

BACKGROUND

Bioprinting enables an automated deposition of living cells together with other components for a development of a three-dimensional (3D) tissue construct. Bioink formulations are created from different sources, including synthetic as well as natural polymers such as collagen, gelatin, alginate, hyaluronic acid, fibrin and polyethylene glycol. It is commonly known that matrix materials used for bioprinting cannot represent the complexity of natural extracellular matrix (ECM), which constitutes a microenvironment for the cells and can modulate cellular processes, including migration, differentiation and other functions. Therefore the presence of ECMs in bioinks is considered beneficial for recreation of a microenvironment with cell-cell connections.

International patent application WO2017014582 reveals a bioink composition comprising 0.05-60×10$^6$/mL of cells, 0.1 to 10 w/v % of a cell carrier material, 0.01 to 1 w/v % of a viscosity enhancer, 1 to 30 v/v % of a lubricant and 0.1 to 10 w/v % of a structural material. The bioink composition may further comprise a tissue-derived component material. Preferably, the cell carrier material is gelatin or collagen, the viscosity enhancer is hyaluronic acid or dextran, the lubricant is glycerol and the structural material is fibrinogen or methacrylated gelatin (GelMa).

The literature comprises many publications regarding the issue of selecting an appropriate bioink composition with optimal properties for tissue engineering applications. Mohamed Ali et al. carried out works on the production of a bioink based on decellularized ECM (dECM) derived from a kidney [1]. A relatively low concentration (1-3%) dECM hydrogel was obtained employing a dissolution method, using 0.5M acetic acid and 0.1 mg/mL pepsin. Additionally, a process of methacrylation of the dECM was carried out with addition of a photoinitiator (Irgacure).

Subsequent research groups attempted to obtain a bioink using ECM adding methacrylated gelatin (GelMa) and a photoinitiator, i.e. LAP (lithium phenyl-2,4,6-trimethylbenzoylphosphinate) [2]. Others used the dECM hydrogel obtained with a relatively high concentration of pepsin with the addition of polycaprolactone (PCL) as a preserving synthetic agent [3].

Patent description KR20180125776 describes a bioink composition comprising a dECM powder and a hydrogel. The dECM powder can be selected form liver tissue, heart tissue, cartilage tissue, bone tissue, adipose tissue, muscle tissue, skin tissue, mucosal epithelial tissue, amniotic tissue, or corneal tissue. Preferably, the dECM powder has a particle size of 0.05 to 100 μm. The hydrogel may contain one or more selected from the group consisting of gelatin, hyaluronic acid, dextran, and collagen.

Falguni et al (2014) developed tissue-specific dECM bioinks, including adipose, cartilage and heart tissues, capable of providing crucial cues for cells engraftment, survival and long-term function. Bioprinting method enabled reconstitution of the intrinsic cellular morphologies and functions. A higher-order assembly of the printed cellular constructs was observed with organized spatial patterns and tissue-specific gene expression. A key advantage of the methodology was the application of tissue specific ECM, providing crucial cues for cells engraftment, survival and long-term function [3].

Experiments involving the decellularization of an organ in order to obtain the dECM as a component of bioink have been studied by many research groups [4, 5, 7]. Various substances were used for decellularization, primarily Triton X-100 and/or dodecyl sulphate (SDS) detergents. A method of decellularization of liver is described in KR1020180011607A, wherein hepatic tissue is treated with a de-saturated solution containing a surfactant and a hyperactive solution. 0.5% of Triton X-100 (Triton X-100) may be used as the surfactant.

Mohamed Ali and colleagues constructed a photo-crosslinkable kidney comprising a ECM-derived bioink [1]. Porcine whole kidneys were decellularized through a perfusion method, dissolved in an acid solution, and chemically modified by methacrylation. The results showed that the bioprinted human kidney cells were highly viable and mature with time. Moreover, the bioprinted renal constructs exhibited the structural and functional characteristics of the native renal tissue. The tissue-specific ECM-derived bioink could enhance the cellular maturation and eventually tissue formation.

Mirmalek-Sani et al (2013) presented the decellularization process of porcine pancreas to create a scaffold for human stem cells and porcine pancreatic islets. Cellular material was effectively removed while preserving ECM proteins and the native vascular system. Moreover, demonstrated that the decellularized pancreas can support cellular adhesion and maintenance of cell functions [6].

SUMMARY

The aim of the aspects of the disclosed embodiments is to provide a detergent-free dECM that could be used in bioprinting. Literature data provides no results on the residual content of detergents in the ECM obtained by decellularization or on the methods assaying their content. In the previously published procedures for decellularization of various tissues, the stage of removal of the detergents is relatively short. It is believed that the absence of the detergent in dECM substantially affects the quality of the dECM obtained. The procedure developed by the applicant allows for almost all of the detergent to be removed without the need of addition of other chemicals. The second aim of the aspects of the disclosed embodiments is to obtain a bioink of a proper consistency and viscosity, without the need of addition of viscosity enhancers.

In a first aspect, there is provided a detergent-free decellularized extracellular matrix (dECM) preparation method comprising the following steps:
  mechanical fragmentation, preferably by mechanical extrusion, of an organ of animal origin selected form pancreas, liver, kidneys, heart, skin, lungs, large intestine, small intestine, blood arteries and veins, adipose tissue and placenta, wherein the organ is separate from the body of the animal incubation of the fragmented organ in a buffered detergent solution, preferably comprising 1× phosphate buffered saline (PBS), whereby the buffered detergent solution comprises 0.5%-1.5%, preferably 1% (v/v), octoxynol-9, wherein the detergent solution is supplemented with an antimicrobial agent, preferably streptomycin, preferably at a concentration of 0.01% (w/v), and the incubation is performed at a temperature below room temperature, preferably at 4° C., for at least 72 h with agitation, wherein the fragmented organ is transferred to a fresh detergent solution every 4 to 12 hours incubation of the fragmented organ in a first buffered washing solution, preferably comprising 1×PBS, whereby the first buffered washing solution comprises an antimicrobial agent, preferably streptomycin, preferably at a concentration of 0.01% (w/v), for at least 72 h at a temperature below room temperature, preferably at 4° C. with agitation, wherein the fragmented organ is transferred to a fresh washing solution every 4 to 12 hours incubation of the fragmented organ in a deoxyribonuclease solution comprising DNAse, preferably at a concentration of 0.0001 to 0,0003% (w/v), most preferably 0.0002% (w/v), preferably for at least 8 hours at a temperature suitable for the DNAse performance incubation of the fragmented organ in a second buffered washing solution, preferably comprising 1×PBS, whereby the second buffered washing solution comprises an antimicrobial agent, preferably streptomycin, preferably at a concentration of 0.01% (w/v), for at least 72 h at a temperature below room temperature, preferably at 4° C. with agitation, wherein the fragmented organ is transferred to a fresh washing solution every 4 to 12 hours freezing of the fragmented organ and crushing the frozen fragmented organ into fragments freeze-drying of the frozen fragmented organ, preferably at −32° C., preferably under a pressure of 0.31 mbar (31 Pa).

optional final drying for 5 to 15 minutes at 0.0010 mbar (0.1 Pa) and −76° C.

grinding the crushed and dried product into 25-500 µm dECM powder optional sterilization of the product, preferably by radiation and/or ethylene oxide Mechanical fragmentation of the organ enhances the removal of the detergent form the organ and results in a product with lower fat content, which improves the properties of the final product, i.e. increases viscosity and improves printability. Addition of DNAse is crucial for removal of the DNA of the organ of animal origin. If the resulting printed three-dimensional structure was comprising dECM with DNA, it could not be further used in transplantation experiments.

Preferably, the grinding step is followed by a step of checking the amount of octoxynol-9 in dECM powder, wherein preferably before dECM powder is checked for the presence of octoxynol-9, it is treated with collagenase, preferably at a concentration of at least 43,953 PZ/g dECM.

Preferably, the grinding step is followed by the following steps:

dissolving of the dECM powder in hydrochloric acid solution, preferably 0.01 M, supplemented with 0-10 mg/ml of pepsin mixing for 48-72 h, preferably for 72 h, at room temperature;

neutralizing on ice, preferably using 0.1 M sodium base and PBS solution.

In a second aspect there is provided a detergent-free decellularized ECM in a powder form, obtainable by the method of preparation of a detergent-free decellularized extracellular matrix (dECM). Preferably, the dECM powder is sterile. If necessary the powder could be sterilized by radiation sterilization or ethylene oxide sterilization.

In a third aspect there is provided a detergent-free decellularized ECM in form of a solution, obtainable by the method of preparation of a detergent-free decellularized extracellular matrix (dECM).

In a fourth aspect there is provided a method of preparation of a primary bioink comprising the following steps:

preparation of a paste comprising 5-50% (w/v), preferably 15-25% (w/v), of the dECM powder according to the second aspect of the disclosed embodiments, and 1-10% (w/v), preferably 8-10% (w/v), of the dECM solution according to the third aspect of the disclosed embodiments by mixing incubation of the paste at a temperature of 7-10° C. for at least 24 hours addition of 1.46-7.32% (w/v) methacrylated gelatin, 0.15-1.10% (w/v) methacrylated hyaluronic acid, 5-10% (w/v) glycerol, and a photoinitiator, preferably 0.03-0.17% (w/v) lithium phenyl-2,4,6-trimethylbenzoylphosphinate, followed by gentle mixing.

Since the dECM powder is originally prepared by freeze-drying and is not dissolved afterwards, it retains the whole quaternary structure of ECM. Hence, use of dECM in the form of a paste, comprising both the dECM powder and the dECM solution, provides the primary bioink with a proper consistency and, since the dECM powder is not dissolved in the primary bioink, it retains the whole quaternary structure of ECM.

In a fifth aspect there is provided the primary bioink comprising a dECM paste and 1.46-7.32% (w/v) methacrylated gelatin, 0.15-1.10% (w/v) methacrylated hyaluronic acid, 5-10% (w/v) glycerol and a photoinitiator, preferably 0.03-0.17% (w/v) lithium phenyl-2,4,6-trimethylbenzoylphosphinate, wherein the dECM paste comprises 5-50% (w/v), preferably 15-25% (w/v), of the dECM powder according to the second aspect of the disclosed embodiments, and 1-10% (w/v), preferably 8-10% (w/v), of the dECM solution according to the third aspect of the disclosed embodiments and wherein the viscosity of the primary bioink is at least 5 Pa·s, measured in a cone-plate system, at a constant shear rate of 21/s and a temperature of 37° C.

The use of dECM makes it possible to reproduce the extracellular conditions of the body, thus giving the bioprint the characteristics of native tissue, which stimulates cells to differentiate and improves their survival rate. Moreover, the extracellular matrix is necessary to obtain a proper viscosity of the bioink and to maintain a stable three-dimensional structure of the printed construct through the additional possibility of thermal cross-linking in the temperature range of 33 to 37° C.

Use of the photoinitiator enables cross-linking, which is non-toxic to cells, as compared to chemical cross-linking using chemicals, which are toxic to cells contained in the primary bioink. Cross-linking with the use of the photoinitiator and visible light minimizes cellular DNA damage as compared to thermal cross-linking. Both temperature and light have negative effects on cells, leading to DNA damage.

However, when cross-linking with visible light, these changes are kept to a minimum.

Methacrylated gelatin (GelMa) is used for shaping of the printed construct. In addition, it brings the filaments together so as to prevent lobule delamination and improves cell and islet viability. GelMa is stable in higher temperatures as compared to gelatin, which is beneficial during thermal cross-linking.

Methacrylated hyaluronic acid (HAMA) helps to maintain the three-dimensional structure by cross-linking. Additionally, HAMA provides smoothness, silkiness, homogeneity of the printed filament and supports cell cultures. These features cannot be obtained by addition of hyaluronic acid, which is not methacrylated.

The use of glycerol improves cell and islet functionality. It also improves the lubricity of the bioink, enables formation of continuous filaments, improves the mixing of bioink components in a syringe or a mixer and reduces the pressure expenditure during printing.

Preferably, the primary bioink comprises at least one additive selected from: hyaluronic acid at a concentration of 0.001 to 0.100 mg/mL of the bioink, preferably, 0.007 mg/mL, laminin at a concentration of 0.005 to 0.100 mg/mL of the bioink, preferably, 0.084 mg/mL, collagen I at a concentration of 0.001 to 0.100 mg/mL of the bioink, preferably 0.041 mg/mL, collagen IV at a concentration of 0.005 to 0.175 mg/mL of the bioink, preferably, 0.122 mg/mL, fibronectin at a concentration of 3 to 300 µg/mL, preferably 100 µg/mL, human fibrinogen at a concentration of 10 to 100 mg/mL of the bioink, aprotinin at a concentration of 1 to 2 EPU/mL of the bioink, polysorbate at a concentration of 0.05 to 2 mg/mL of the bioink, human thrombin at a concentration of 5 to 55 mg/mL of the bioink, calcium chloride at a concentration of 20 to 60 mM/mL of the bioink; proangiogenic vitamins: vitamin A at a concentration of 1 nM-500 µM, preferably 100 µM, vitamin B1 at a concentration of 50-100 µM, preferably 100 µM, vitamin B3 at a concentration of 1 to 10 µM, preferably 10 µM, vitamin B12 at a concentration of 10 to 100 mg/mL of the bioink, vitamin D3 at a concentration of 0.1 to 10 nM, preferably 10 nM, growth factors supporting angiogenesis: VEGF at a concentration of 10 to 30 ng/mL of the bioink, preferably 30 ng/mL, FGF at a concentration of 10 to 20 ng/mL of the bioink, preferably 20 ng/mL, TGF-$\beta$ at a concentration of 1 to 10 ng/mL of the bioink, preferably 20 ng/mL, interleukin (IL)-8 at a concentration of 0 to 100 ng/mL of the bioink, preferably 10 ng/mL, IL-17A at a concentration of 20 to 50 ng/mL of the bioink, preferably 20 ng/mL.

Commercial additives such as hyaluronic acid, collagen I and IV and laminin further improve the functionality of the printed three dimensional structure.

Vitamin A—ATRA (All Trans Retinoic Acid) as one of the metabolites of vitamin A has a proangiogenic effect—it improves the expression of the factors behind angiogenesis (e.g. cyclooxygenase-2 (COX-2), hypoxic-induced factor (HIF)-1, C-X-C, chemokine receptor (CXCR)-4, vascular endothelial growth factor (VEGF), angiotensin (Ang)-2, -4. Moreover, it has been demonstrated that ATRA reduces pro-MMP2 (pro-matrix metalloproteinase-2—type IV collagenase) activity.

Vitamin B1—benfotiamine (a thiamine derivative) inhibits apoptosis on the protein-dependent B-kinase pathway (PKB/Akt) and is responsible for inducing the proliferation of progenitor endothelial cells.

Vitamin B3—niacin, through its receptor, i.e. hydroxycarboxylic acid receptor 2 (GPR109A), enhances and promotes endothelial cell functions that support angiogenesis. Moreover, vitamin B3 is a precursor of NAD(+), which by way of response with a sirtuin mediator (SIRT), induces and supports vessel formation.

Vitamin B12 (cobalamin) induces the production of prostaglandins E1, prostacyclins and nitric oxide (NO). All of these substances have a favourable effect on the onset of angiogenesis.

Vitamin D3 is designed to stimulate angiogenesis in vitro. It induces increased expression of VEGF and pro-MMP2 activity. It also affects the function of ECFC (endothelial colony forming cells).

VEGF induces proliferation, migration, sporulation and formation of connections between endothelial cells, and, in addition, by inducing the production of various proteases, affects the degradation of extracellular matrix (ECM) and activates cell surface integrins of endothelial cells.

Fibroblast Growth Factor (FGF) increases endothelial cell migration and promotes capillary morphogenesis. It also increases endogenous VEGF production.

Transforming Growth Factor (TGF-$\beta$) promotes the formation of ECM (proteoglycans, fibronectin, collagen), regulates the proliferation of endothelial cells, their migration and formation of blood vessels. TGF-$\beta$ mediates the interactions of endothelial cells and pericytes.

Interleukin (IL)-8 has a potent proangiogenic effect on endothelial cells by interacting with CXCR1 and CXCR2 receptors. It stimulates the formation of a microvascular network.

IL-17A—Induces angiogenesis, cell migration and cytoskeleton rearrangement.

Preferably, the primary bioink comprises one or more animal- or human-derived additives selected from endothelial cells at a density of $0.1\text{-}10 \times 10^5$/mL of the bioink, primary microvascular endothelial cells at a concentration of 0.1 to $10 \times 10^5$/mL of the bioink, animal- or human-derived $\alpha$ cells at a concentration of 3 to $9 \times 10^6$/mL of the bioink, animal- or human-derived $\beta$ cells at a concentration of 1.1 to $3.4 \times 10^7$/mL of the bioink, animal- or human-derived pancreatic islets, preferably in the amount of 20,000 iEq/mL of the bioink.

Pancreatic islets are responsible for insulin production. Endothelial cells are added for a faster formation of a vascular network in the printed three-dimensional structure. Primary microvascular endothelial cells are used to support the formation and growth of microvessels in the bioprinted three-dimensional structure.

In a sixth aspect there is provided a method of preparation of a vascular bioink comprising the steps of:

a) optional preparation of a solution of microbiological gelatin supplemented with CMC comprising preparation of a 1-2% (w/v) solution of microbiological gelatin in a buffer solution, preferably PBS, by suspending microbiological gelatin in the buffer solution with agitation at a temperature between 50 and 65° C., preferably at 60° C., addition of a 2-5% (v/v) carboxymethyl cellulose (CMC) aqueous solution to obtain a final concentration of 0.2-1% (v/v) of CMC in the bioink and cooling the solution to a temperature equal or below 40° C.

b) preparation of a 5-10% (w/v) dECM solution by addition of dECM powder according to the second aspect of the disclosed embodiments, preferably sterilized by radiation, to (i) the solution of microbiological gelatin supplemented with CMC obtained in step a) or (ii) a buffer solution or (iii) a solution of cell medium with gentle agitation.

c) sonication of the obtained solution at a temperature not exceeding 37° C. for 0.5-2.0 hours d) optional addition of at least one animal- or human-derived additive selected from: fibronectin at a concentration of 3 to 300 µg/mL, preferably 100 µg/mL, VEGF at a concentration of 10 to 30 ng/mL, preferably 30 ng/mL, FGF at a concentration of 10 to 20 ng/mL, preferably 20 ng/mL, PGE2 at a concentration between 100 and 300 nM, preferably 100 nM, endothelial cells at a density of between 0.1 and $10 \times 10^7$ cells/mL of the bioink, fibroblasts at a density of between 0.1 and $10 \times 10^6$ cells/mL of the bioink.

In a seventh aspect there is provided a method of preparation of a vascular bioink comprising the steps of:

a) optional preparation of a solution of microbiological gelatin supplemented with CMC comprising preparation of 1-5% (w/v) solution of microbiological gelatin in a buffer solution, preferably PBS, by suspending microbiological gelatin in the buffer solution with agitation at a temperature between 50 and 65° C., preferably at 60° C., addition of a 2-5% (v/v) aqueous CMC solution to obtain a final concentration of 0.2-2% (v/v) of CMC in the bioink and cooling the solution to a temperature equal or below 40° C.

b) preparation of a 2-10% (w/v) dECM solution by addition of dECM powder according to the second aspect of the disclosed embodiments, preferably sterilized by radiation, preferably sterilized by radiation, to (i) the solution of microbiological gelatin supplemented with CMC obtained in step a) or (ii) a buffer solution or (iii) a solution of cell medium to with gentle agitation.

c) boiling the mixture at 100° C. for 15-30 minutes d) optional addition of at least one animal- or human-derived additive selected from: fibronectin at a concentration of 3 to 300 µg/mL, preferably 100 µg/mL, VEGF at a concentration of 10 to 30 ng/mL, preferably 30 ng/mL, FGF at a concentration of 10 to 20 ng/mL, preferably 20 ng/mL, PGE2 at a concentration between 100 and 300 nM, preferably 100 nM, endothelial cells at a density of between 0.1 and $10 \times 10^7$ cells/mL of the bioink, fibroblasts at a density of between 0.1 and $10 \times 10^6$ cells/mL of the bioink.

In an eighth aspect there is provided the vascular bioink comprising sonicated or boiled dECM solution according to the third aspect of the disclosed embodiments mentioned above at a concentration of 2-10% (w/v), preferably supplemented with microbiological gelatin at a concentration of 1 to 5% (w/v) and/or CMC at a concentration of 0.2 to 2% (v/v).

The sonicated or boiled dECM changes its physical and chemical properties with temperature changes. This component is designed to ensure proper viscosity of the bioink during printing at a relatively low temperature (15-20° C.) and to preserve the printed duct until cells infiltration as well as slow liquefaction at the culture temperature of 37° C.

Microbiological gelatin provides a desired consistency and improves cell survival rate. CMC increases viscosity and stabilises bioink consistency. Fibronectin promotes angiogenesis and depending on the dose, stimulates elongation of the vessels formed without affecting the proliferation rate.

Preferably, the vascular bioink comprises at least one animal- or human-derived additive selected from: fibronectin at a concentration of 3 to 300 µg/mL, preferably 100 µg/mL, VEGF at a concentration of 10 to 30 ng/mL, preferably 30 ng/mL, FGF at a concentration of 10 to 20 ng/mL, preferably 20 ng/mL, PGE2 at a concentration between 100 and 300 nM, preferably 100 nM, endothelial cells at a density of 0.1 and $10 \times 10^7$ cells/mL of the bioink, fibroblasts at a density of between 0.1 and $10 \times 10^6$ cells/mL of the bioink.

Endothelial cells produce blood vessels. Fibroblasts produce angiogenesis-inducing factors. VEGF induces proliferation, migration, sporulation and formation of connections between endothelial cells. Moreover, by inducing the production of various proteases, VEGF affects the degradation of the ECM and activates cell surface integrins of endothelial cells. FGF increases endothelial cell migration and promotes capillary morphogenesis. It also increases endogenous VEGF production. PGE2—prostaglandin E2, designed to induce migration, proliferation and formation of new vessels by activating (phosphorylation) FGF of the (R)-1 receptor.

In a ninth aspect there is provided a three-dimensional structure comprising at least three adjacent bioink layers, wherein a layer of the vascular bioink according to the eight aspect of the disclosed embodiments is arranged between two layers of the primary bioink according to the fifth aspect of the disclosed embodiments.

In a tenth aspect there is provided a method of preparation of a three-dimensional structure, wherein the primary bioink according to the fifth aspect of the disclosed embodiments and the vascular bioink according to the eight aspect of the disclosed embodiments are deposited layer by layer in a 3D-bioprinting process at a printing speed from 5 to 50 mm/s, pressure from 4 to 300 kPa and temperature from 4 to 37° C. and wherein during or after deposition the primary bioink is exposed to UV light and/or visible light, preferably of the wavelength form 365 to 405 nm, more preferably at 405 nm, for at least 5 seconds. Cross-linking at 405 nm is preferred, as it is not toxic for the cells contained in the three-dimensional structure.

The aspects of the disclosed embodiments enabled obtaining of a model of a lobule 27×17×2.5 mm in size. A lobule consisting of 5 layers was printed in 3-10 minutes. Additionally, a 3D model of a functional organ prototype 30×40× 20 mm in size was obtained. The model consisted of 30 layers and was printed in 20 to 60 minutes. Also importantly, this is the first time that boiled or sonicated dECM use is reported. The aspects of the disclosed embodiments enable obtaining a construct in a short time due to the printing speed being properly correlated with the viscosity of bioink (up to 30 mm/s). A stable three-dimensional porous structure can be obtained (30 layers), which is preservable at a temperature of 37° C. for 20 days. In a preferred embodiment, the primary bioink is based on using a less toxic photoinitiator, i.e. LAP rather than Irgacure at a relatively low concentration. Moreover, a smaller amount of pepsin is used than found in the literature to obtain dECM solution.

Figure 1:
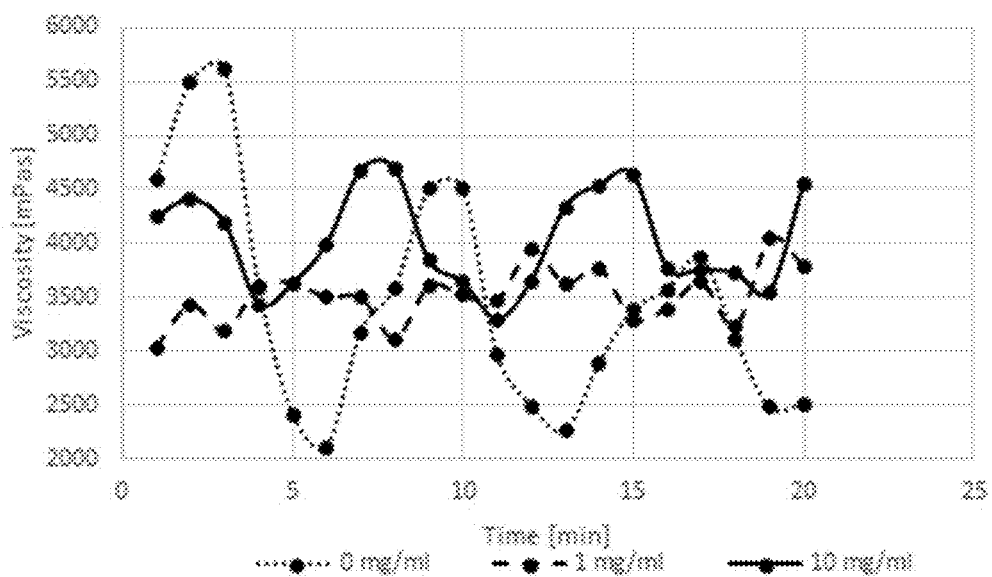
FIG. 1. Influence of pepsin concentration on the properties of dECM hydrogel

A)-C)—SEM (scanning electron microscopy) images; A) native tissue before decellularization; B) tissue after decellularization; C) construct printed from primary bioink.

D)-E) —TEM (transmission electron microscopy) images; D) tissue after decellularization; E), F) constructs printed from the primary bioink with preserved collagen quaternary structure (visible collagen fibres).

DETAILED DESCRIPTION OF THE EMBODIMENTS

Embodiment 1: Preparation of the Detergent-Free dECM

A. Procedure for the Decellularization of the Pancreas

1% (v/v) Triton X-100 solution with 0.1% (v/v) ammonia water in 1× concentrated PBS solution with 0.01% (w/v) streptomycin was prepared for removing cell structures from the pancreatic organ while leaving the extracellular matrix (scaffold). After harvesting, the tissue material was frozen at −80° C. Then, after thawing, the outer layer of fat tissue and the surrounding membranes were removed from the organ. The prepared pancreases were treated in two ways: cut into small pieces (about 1-1.5 cm) and mechanically ground (using an extrusion grinding method).

The fragmented tissue was placed in a bottle and suspended in a previously prepared solution of Triton X-100. The specimens were placed in an incubator at 4° C. at constant agitation of 150 rpm. Every 4 h to 12 h, the detergent was replaced until the cellular fraction was completely removed (3-5 days). The detergent was then washed out from the scaffold obtained. For this purpose, a solution of 1×PBS with 0.01% (w/v) streptomycin was used. The washing process was carried out for 72 h at 4° C. with continuous stirring at 150 rpm.

The next stage—decellularization—consisted in administering a deoxyribonuclease solution (0.0002% (w/v) DNAse in 1×PBS, supplemented with 0.12 mM calcium and magnesium ions). The scaffold was incubated in the abovementioned solution for 8 hours at 37° C. with stirring at 150 rpm. The last step involved washing again with 1×PBS solution with 0.01% (w/v) streptomycin at standard conditions (4° C.; 150 rpm; 72 h). In addition, washing out of the detergent using ammonia water at a concentration of 0.1% (v/v) in 1× concentrated PBS solution was also tested. Moreover, the effect of an increase in temperature to 20-24° C. on the washing step was studied.

After the end of the decellularization process, the scaffold obtained was frozen in liquid nitrogen and crushed into pieces of approx. 0.5 cm in size. The material was freeze-dried for 26 h at a temperature of −32° C. and 0.31 mbar (31 Pa) pressure. The final drying process lasted 10 minutes at 0.0010 mbar (0.1 Pa) pressure and temperature of −76° C. The crushed and dried scaffold was ground into powder using a cryogenic mill. The grinding procedure involved 3 cycles for 1 minute at 15 impacts per second.

In order to characterise the product obtained, i.e. dECM powder abbreviated as "dECM(p)", powder grain size distribution in flow gradient was tested using a laser diffraction spectrometer Spraytec (Malvern, UK) equipped with an accessory inhalation chamber for studying inhalation sprays. In all the cases studied, the values of the parameters describing the analysed powder following aerosolization were comparable, indicating that there was no need to provide additional energy in the form of an increased air stream to break down the powder into individual particles. Table 1 presents the values of parameters describing the diameters of powder particles, where:

Dv(50) —median of the volume particle size distribution: the diameter of the particles that divides the cumulative volume distribution in half, in other words, all particles both smaller and larger than the median have the same volume (the particles below this diameter constitute 50% of the sample volume).

Dv(10) —the particles below this diameter constitute 10% of the sample volume.

Dv(90) —the particles below this diameter constitute 90% of the sample volume.

D[3][2]—the Sauter diameter is the diameter of a particle whose volume to surface ratio is the same as the ratio of the volume of all analysed particles to the surface of the total of all such particles.

D[4][3]—a diameter defined as the ratio of the sum of the fourth power of particle diameters to the sum of the third power of particle diameters.

TABLE 1

Values of parameters describing the diameters of powder particles

| Flow [l/min] | Parameter | Diameter [μm] | SD [μm] |
|---|---|---|---|
| 100 | Dv(10) | 28.23 | 1.48 |
| | Dv(50) | 148.43 | 10.14 |
| | Dv(90) | 410.1 | 29.41 |
| | D[3][2] | 54.19 | 4.54 |
| | D[4][3] | 189.6 | 12.4 |
| 200 | Dv(10) | 27.7 | 5.7 |
| | Dv(50) | 139.7 | 27.2 |
| | Dv(90) | 474.4 | 123.8 |
| | D[3][2] | 43.4 | 5.2 |
| | D[4][3] | 202.1 | 40.1 |
| 270 | Dv(10) | 25.3 | 2.2 |
| | Dv(50) | 146.7 | 25.6 |
| | Dv(90) | 498.3 | 62.7 |
| | D[3][2] | 46.3 | 4.6 |
| | D[4][3] | 209.5 | 27.5 |

The results of the measurements following the aerosolization of the dECM powder indicate that the powder was polydispersible. The median of the volume particle diameter distribution—Dv(50) at an air flow nominal for Cyclohaler type inhaler equaled 148.43±10.14 μm. At the same time, the smallest particles of the total volume not exceeding 10% of the total volume of the sample had a diameter of less than 28.23±1.48 μm (Dv(10)), while the diameter distinguishing the particles with total volume less than 90% of the total volume of the sample was 410.10±29.41 μm. Increasing the air flow rate fed to the inhaler to 200 and 270 $dm^3$/min did not significantly affect the value of the median of the volume particle size distribution or the Dv(10) value. Only a slight increase in the size of the largest particles (Dv(90)) from approx. 410.1±29.41 μm to 498.3±62.7 μm could be observed. This resulted in an increase in the distribution span from 2.57±0.04 (for 100 $dm^3$/min flow) to 3.3±0.4 (for 270 $dm^3$/min flow).

B. Efficacy of the Decellularization Method

Protein Characteristics of the Product:

Using the mass spectrometry technique, the ECM protein composition after decellularization of the porcine pancreas was determined. The results obtained clearly demonstrated the highest percentage of collagens in the samples tested, with collagen type 1 (COL1) of the alpha (A)-1 chain, the so-called COL1A1, showed the highest values compared to the other detected collagen types.

TABLE 2

The percentage of COL1A1 in the samples tested. Ml8, M22, M23, M24s, M24, M25 denote the sample number.

| | control | M18 | M22 | M23 | M24s | M24 | M25 |
|---|---|---|---|---|---|---|---|
| % (w/w) of COL1A1 in the sample | 0.001 | 99.5 | 91.4 | 99.5 | 94.3 | 92.6 | 99.3 |

Also, significant amounts of type IV and type VI collagen were found. This shows that the decellularization protocol used allowed for preserving the types of collagen that have the highest level of integration with pancreatic islets and 13 cells. Type I and type IV collagen is the most effective in supporting the functionality and viability of pancreatic islets and they are commonly used as supplements in biomedical applications that are based on the functioning of pancreatic islet cells. Notably, collagen VI and IV are present on the extra secretory surface and basement membrane of pancreatic islets and they regulate fibronectin activity. The percentage content of any of other collagen types analysed (COL1A2, COL3A1, COL4A2, COL6A1, COL6A2, COL6A3 COL14A1) did not exceed 3.5% in all examined samples.

Final DNA Concentration

In order to determine the residual DNA concentration, three analyses were carried out:

(a) PicoGreen to determine residual DNA concentration.

(b) Agarose gel electrophoresis to determine the particle size of the remaining genetic material.

(c) Microscopic imaging—haematoxylin & eosin (H&E) staining.

The decellularization process has been successfully completed when the concentration of residual DNA did not exceed 50 ng of double-stranded DNA (dsDNA) per mg ECM of dry weight, and the molecules of the remaining DNA did not exceed 200 base pairs (bp). Also, the microscopic image of the scaffold obtained was evaluated for the presence of cell nuclei (haematoxylin & eosin staining).

The concentration of residual DNA in the dry matter was on average 0.077 ng/mg. In all examined samples the residual DNA content was lower than 0.15 ng/mg. The analysis was carried out using DNeasy Blood & Tissue Kit kits used to isolate residual DNA, and Quant-iT PicoGreen dsDNA Reagent and Kits to determine the concentration of the isolated genetic material.

No signal was found using agarose gel electrophoresis. All samples were below the detection level, which clearly demonstrates that ECM had no residual DNA in the form of particles larger than 200 bp.

Microscopic examination showed no genetic material, no cell nuclei were visible following the decellularization process.

Triton X-100 Residue and Effective Method for the Detection and Removal Thereof

For comparison, decellularization with 0.5% (w/v) SDS was conducted. The result, however, was not satisfactory due to the large quantities of detergent remaining in the final product. ECM powder showed high foaming level when attempts were made to dissolve it. This was not observed with the use of Triton X-100.

In order to verify the concentration of Triton X-100 remaining after the decellularization process, its residue in the final product was determined.

Preparation of the Samples for Analysis:

Given the white colour of the dissolved dECM, the samples were treated with three concentrations of collagenase: 4.3953 PZ activity units/g dECM(p), 43.953 PZ/g dECM(p) and 87.906 PZ/g dECM(p). Collagenase was prepared in a special solution containing 150 mL of Ringer's solution pH 7.2 to 7.4, 2.72 mL Hepes (1M), 1.125 mL NaBicarbonate (7.5%) and 1.05 mL $CaCl_2$) (1M).

The samples were stirred for 24 h at 37° C. with a constant function of shaking at 1000 rpm. The solutions obtained were analysed for residual concentration of non-ionic detergent Triton X-100. Sample A was the result of treating dECM with a single collagenase concentration. Sample B was treated with 10-fold collagenase concentration. Sample C was treated with 20-fold collagenase concentration (A=6.977 μg Triton X-100/g dECM(p), B=40.475 μg Triton X-100/g dECM(p), C=39.325 μg Triton X-100/g dECM(p)).

Importantly, the highest concentration of the remaining Triton X-100 was found in the dECM solution treated with collagenase at a concentration of 43,953 PZ/g dECM. An increase in the concentration of collagenase did not result in a higher amount of Triton X-100 obtained, which indicated that the concentration of 43,953 PZ/g of dECM was sufficient for extraction of all the remaining Triton X-100 from the sample.

Previous published attempts to evaluate this detergent did not yield any tangible results for the following reasons:
- the evaluation of Triton X-100 powder was impossible since that form of ECM absorbed the dye and thus distorted the result. This correlation was demonstrated by analysing ECM powder after decellularization with a SDS detergent, which indicated the presence of Triton X-100, which was not possible due to the detergent used.
- the dECM, dissolved in pepsin and neutralized, due to its white colour, prevented the readout of the concentration.

Therefore, treating dECM with collagenase is hitherto the only method for evaluating the residue of detergents in biological material following decellularization. This is of importance where such material (dECM) was to be used in the bioprinting process with viable cells. This is crucial if such material was to be used for implantation in humans.

C. Results

In the first step, the differences in fat composition in decellularized matrix in the function of the preparation of pancreas for decellularization were analysed. In the next step, the content of residual DNA, depending on the method of pancreatic preparation, collagen content and the content of residual detergent Triton X-100 were analysed.

The use of the mechanical extrusion grinding method allowed for significantly reducing the fat content in the extracellular matrix obtained. In the mechanical extrusion grinding method, the fat content was 6.24+/−0.07% (w/w) compared to 21.47+/−0.07% (w/w) of the fat content in the cutting method. The difference was statistically significant ($p<0.001$). Low fat content of obtained dECM significantly increased the viability of cells and pancreatic islets.

The content of residual DNA tested with Picogreen was significantly lower when using the mechanical extrusion grinding, namely 0.07+/−0.07 ng/mg compared to 0.13+/−0.06 ng/mg of tissue ($p=0.027$). This was in both cases well below the permissible 50 ng/mg value.

The use of the mechanical extrusion grinding method allowed for significantly reducing Triton X-100 content in the extracellular matrix obtained. In the mechanical extrusion grinding method, the detergent content was 3.79+/−2.33 µg/g as compared to 6.53+/−2.34 µg/g in the cutting method. The difference was statistically significant ($p=0.008$).

The content of collagens in the tested material resulting from the preparation method did not differ depending on the use of the cutting method and mechanical extrusion grinding.

The use of ammonia water to alkalize the environment for better washing out Triton did not result in improved washing out of Triton. It brought about, however, a change in the composition of the collagens obtained. Similarly, washing at 24° C. failed to improve washing out of Triton, while increasing the damage to collagen structures and resulting in obtaining higher results of DNA content, which could indicate the risk of infection of the material. Therefore, the optimal method was to wash the decellularized material in PBS at a temperature of 4° C. for 72 hours.

Embodiment 2: Preparation of Bioinks

A. dECM(p) Dissolution

In order to obtain a dECM solution (dECM(r)), a dECM powder (dECM(p)) dissolution procedure has been established that used pepsin and hydrochloric acid (HCl).

The procedure for obtaining the dECM solution was divided into two parts:

(a) Dissolving of dECM.

Pepsin (at a concentration of 0-10 mg/mL, preferably 1 mg/mL) was dissolved in 50 ml of 0.01 M HCl, after which dECM(p) (0.5-5 g) was added. This method resulted in a dECM(r) concentration in the range of 1-10% (w/v). The prepared solution was placed on a magnetic stirrer, using the following stirring conditions: ambient temperature of approx. 25° C., dissolution time of 72 h, wherein the solution was agitated every hour for the first 8 h of stirring.

(b) Neutralisation of dECM(r).

Neutralization of 50 mL of dECM(r) was carried out on ice (the desired temperature of the dECM solution was 4 to 4.5° C.) to pH 7.2-7.4 using the following substances:
- 5 ml 0.1 M NaOH (the volume of 0.1 M NaOH was equal to 1/10 of the volume of dECM(r) for neutralization);
- 5.56 mL 10×PBS (the volume of 10×PBS was equal to 1/9 of the volume of dECM(r) for neutralization);
- a suitable volume of 1×PBS (1-10 ml) was used to dilute the dECM solution.

In order to identify the procedure appropriate for the preparation of dECM(r), analysis was carried out of solutions with a relatively high concentration of dECM(p) ground after radiation sterilization—10% (w/v) with varying pepsin content.

dECM solutions with varying pepsin content were prepared. The solution containing 1 mg/mL pepsin had relatively high homogeneity: a small span of viscosity values. A slight change in turbidity was observed with the temperature change. All analysed dissolution methods with varying pepsin content were used for the preparation of dECM(r), however, it was demonstrated that the amount of 1 mg/mL used was optimal.

B. Preparation of the Bioinks (a) Conditions for Obtaining the Primary Bioink:
- Neutralised dECM solution with dECM(p) ground, cut, with and without radiation sterilisation or ethylene oxide sterilization
- dECM(p) powder ground, cut, with and without radiation sterilization or ethylene oxide sterilization
- Sterile GelMa 10-20% (w/v) with 0.2-0.5% (w/v) LAP
- Sterile HAMA 1-3% (w/v) with 0.2-0.5% (w/v) LAP
- Sterile glycerol
- Culture medium 1:5-7 v/v, pancreatic islets 20,000 iEq/mL and cell lines: endothelial cells $1 \times 10^5$/mL, primary microvascular endothelial cells $1 \times 10^5$/mL, vitamins A—100 µM, B1—100 µM, B3—10p, D3—10 nM, growth factors: VEGF—30 ng/mL, FGF—20 ng/mL, tumour necrosis factor (TNF)-α—10 ng/mL, IL-8—10 ng/mL, IL-17A—20 ng/mL.

First, a paste was prepared containing an appropriate amount of neutralised dECM(r) and dECM(p) by thorough mixing with a sterile metal spatula. Since the dECM(p) was prepared by freeze-drying and was not dissolved afterwards, it retained the quaternary structure of ECM. The paste obtained was left at a temperature of 7-10° C. for at least 24 h. Directly before using the paste for bioink production, it was placed in a sterile syringe and mixed between syringes. At the same time, GelMa (10-20% (w/v)) and HAMA (1-3% (w/v)) solutions were prepared with LAP according to a commonly available procedure. The syringe containing the paste was attached with a connector to another syringe without the piston, which was moved upside down and stably arranged in the vertical position. Glycerol, culture medium, growth factors, vitamins, GelMa and HAMA solutions were successively added. The piston was then gently inserted, and the paste was mixed with the other reagents. After mixing, the prepared bioink was placed in the incubator for 5 minutes, islets and cells were added, then mixed again and introduced into a cartridge. In the next step, the filled cartridge was centrifuged for 2 minutes in 1500 rpm and reintroduced before printing for approx. 5 minutes to the incubator.

The compositions of the obtained primary bioinks were the following: 40-50% (v/v) of dECM(r), 2.763-27.692% (w/v) of dECM(p), 1.464-7.320% (w/v) of GelMa, 0.146-1.098% (w/v) of HAMA, 5.0-10.0% (w/v) of glycerol, 0.03-0.17% (w/v) of LAP, VEGF—30 ng/mL, FGF—20 ng/mL, TGF-β—10 ng/mL, IL-8—10 ng/mL, IL-17A—20 ng/mL, vitamin A—100 µM, vitamin B1—100 µM, vitamin B3—10 µM, vitamin D3—10 nM, pancreatic islets—20000 iEq/mL, endothelial cells—1×10$^5$/mL, primary microvascular endothelial cells—1×10$^5$/mL.

(b) Vascular Bioink

The process of vascular bioink production using sonication was divided into two steps:

Preliminary dissolution—a suitable amount of microbiological gelatin was suspended in PBS (1 to 2% (w/v)) and stirred with a magnetic stirrer for about 10 minutes at 60° C. Then, with constant stirring, the temperature was reduced and dECM(p), ground and cut after and without radiation sterilization or ethylene oxide sterilization was added in batches (5 to 10% (w/v)) and the solution was additionally stirred every 2 minutes. Depending on the variant, a previously prepared PBS-based carboxymethyl cellulose (CMC) solution (2 to 5% (v/v)) was added to the mixture.

Sonication: a bottle with the prepared ECM solution was placed in a beaker with ice, after which a sonicator head and a temperature sensor were placed therein and the sonication process was conducted following a developed procedure using 3 s pulses with an amplitude of 45%, while stopping work at a temperature above 30° C. signalled by an alarm. Sonication was conducted for 0.5 to 2.0 h.

Alternatively, the preliminary dissolution step was omitted and a 5-10% (w/v) dECM solution was prepared by addition of dECM powder to a buffer solution or a solution of cell medium with gentle agitation. Next, the sonication step was performed as described above.

The process of producing vascular bioink by boiling was divided into two steps:

Preliminary dissolution—a suitable amount of microbiological gelatin was suspended in PBS (1 to 5% (w/v)) and stirred with a magnetic stirrer for about 10 minutes at 60° C. Then, with constant stirring, the temperature was reduced and dECM(p), ground and cut after and without radiation sterilization or ethylene oxide sterilization was added in batches (2 to 10% (w/v), and the solution was additionally stirred every 2 minutes. Depending on the variant, a previously prepared PBS-based CMC solution (2 to 5% (v/v)) was added to the mixture.

Boiling: a bottle with the prepared ECM solution or ECM powder (5 to 10% (w/v)) in PBS solution was placed on a magnetic stirrer equipped with a heating plate heated to 100° C., where the mixture was boiled over 15 to 30 minutes.

Alternatively, the preliminary dissolution step was omitted and a 5-10% (w/v) dECM solution was prepared by addition of dECM powder to a buffer solution or a solution of cell medium with gentle agitation. Next, the sonication step was performed as described above.

Vascular bioink's bases thus prepared were supplemented with fibronectin, growth factors and endothelial cells.

The composition of the obtained sonicated vascular bioink was as follows: 5-10% (w/v), preferably 7.5% (w/v) of dECM(p), 0.2-1% (v/v) of CMC, 1—2% (w/v), preferably 1% (w/v) of microbiological gelatin, fibronectin—100 µg/mL, VEGF—30 ng/mL, FGF—20 ng/mL, PGE2—100 nM, 1.5×10$^7$/mL of endothelial cells and 3×10$^6$/mL of fibroblasts.

The composition of the obtained boiled vascular bioink was as follows: 2-10% (w/v), preferably 5% (w/v) of dECM (p), 0.2-2% (v/v) of CMC, 1-5% (w/v), preferably 1% (w/v) of microbiological gelatin, fibronectin—100 µg/mL, VEGF—30 ng/mL, FGF—20 ng/mL, PGE2—100 nM, 1.5×10$^7$/mL of endothelial cells and 3×10$^6$/mL of fibroblasts.

Alternatively, the vascular bioink consisted of 5-10% (w/v), preferably 5% (w/v) dECM(p) in a buffer solution or a cell medium.

Embodiment 3: Characteristics of the Primary Bioink

A. Rheology

The tests conducted served as a basis to determine the values of characteristic parameters, constituting factors limiting the possibility of using a particular system for printing a pancreas lobule model—viscosity value of more than 5 Pa·s. The influence of pepsin concentration on the properties of dECM hydrogel is presented below.

TABLE 3

The effect of temperature (25-37° C.) on turbidity of dECM (r)

| | Pepsin concentration [mg/mL] | | |
|---|---|---|---|
| | 0 | 1 | 10 |
| T [° C.] | Absorbance [—] | | |
| 25 | 2.241 | 2.3565 | 2.437 |
| 26 | 2.2415 | 2.356 | 2.4365 |
| 27 | 2.2415 | 2.356 | 2.4365 |
| 28 | 2.242 | 2.356 | 2.4355 |
| 29 | 2.2425 | 2.356 | 2.435 |
| 30 | 2.2425 | 2.3555 | 2.435 |
| 31 | 2.242 | 2.3555 | 2.434 |
| 32 | 2.242 | 2.3555 | 2.4325 |
| 33 | 2.2425 | 2.355 | 2.4315 |
| 34 | 2.2425 | 2.3545 | 2.4295 |
| 35 | 2.2425 | 2.3535 | 2.428 |
| 36 | 2.242 | 2.353 | 2.424 |
| 37 | 2.242 | 2.352 | 2.4215 |

TABLE 4

The influence of exposure time to the temperature of 37° C. on turbidity of dECM (r)

| | Pepsin concentration [mg/mL] | | |
|---|---|---|---|
| | 0 | 1 | 10 |
| t [min] | Absorbance [—] | | |
| 0 | 2.2875 | 3.1455 | 2.8155 |
| 10 | 2.282 | 3.131 | 2.8075 |
| 20 | 2.2755 | 3.118 | 2.786 |
| 30 | 2.2695 | 3.1005 | 2.769 |
| 40 | 2.267 | 3.0885 | 2.7585 |
| 50 | 2.265 | 3.081 | 2.752 |
| 60 | 2.2635 | 3.0725 | 2.7455 |
| 70 | 2.2625 | 3.0685 | 2.7415 |
| 80 | 2.262 | 3.065 | 2.7365 |
| 90 | 2.261 | 3.0605 | 2.732 |
| 100 | 2.261 | 3.0585 | 2.7295 |
| 110 | 2.2595 | 3.0545 | 2.727 |
| 120 | 2.259 | 3.052 | 2.7225 |

TABLE 5

The influence of pepsin concentration on viscosity of dECM (r), measured for 50 min for constant shear rate (2 1/s)

| Pepsin concentration [mg/mL] | η [mPa · s] |
|---|---|
| 0 | $2109.7 < \eta < 5611.9$ |
| 1 | $3026.9 < \eta < 4040.7$ |
| 10 | $3287.6 < \eta < 4691.3$ |

In order to identify the composition of the bioink with optimal properties, the viscosity of dECM solutions and pastes was tested using the MCR 72 rheometer (Anton Paar) following a specially developed procedure to represent the conditions existing during bioprinting: cone-plate system, constant shear rate of 21/s and the test temperature of 37° C. The results of system rheology testing taking into account the differences in samples by the type of powder used (MS—ground and sterilised, CS—cut and sterilised, MNS—ground, not sterilised, CNS—cut, not sterilised), and the concentration of components used are presented in FIG. 2.

Figure 2:
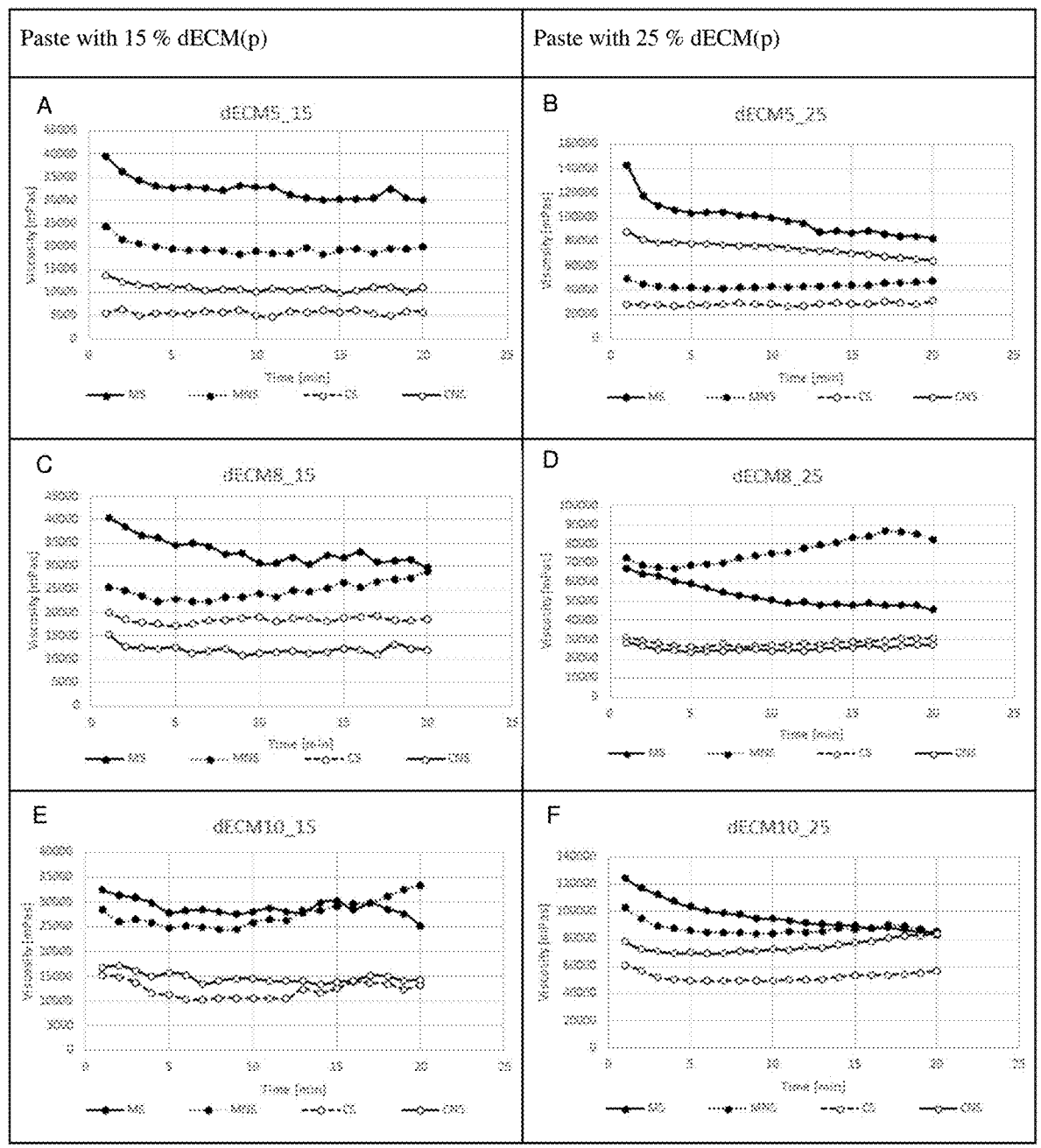
FIG. 2. A relationship between the concentration of dECM solutions and viscosity of A) 5% (w/v) dECM solution supplemented with 15% (w/v) dECM powder, B) 5% (w/v) dECM solution supplemented with 25% (w/v) dECM powder, C) 8% (w/v) dECM solution supplemented with 15% (w/v) dECM powder, D) 8% (w/v) dECM solution supplemented with 25% (w/v) dECM powder, E) 10% (w/v) dECM solution supplemented with 15% (w/v) dECM powder, F) 10% (w/v) dECM solution supplemented with 25% (w/v) dECM powder.

An increase in the concentration of dECM solutions results in an increase in viscosity [FIG. 2]. The viscosity values obtained seem to be too low to allow for using the dECM(r) as an agent conferring proper consistency to the bioink. The solutions obtained with the dECM(p) subjected to sterilisation in each case under consideration had lower viscosity values than non-sterile powder solutions. A slight difference in the solution consistency was observed for the use of ground and cut powder in lower dECM(r) concentrations. For 10% (w/v), ground powder dECM(r) was slightly more viscous than dECM(r) prepared from cut dECM(p).

The summary of the results shows that the use of the dECM paste was necessary to obtain a bioink base having a suitable consistency. All the systems from the summary have a viscosity within the range acceptable for use during printing. Moreover, it seems expedient to use for bioprinting a mixture of components with cells and islets using sterile powder, following sterilisation.

Addition of glycerol into the primary bioink (paste) caused a slight decrease in viscosity of the primary bioink, contrary to the literature data, reporting an increase of viscosity of bioinks upon addition of glycerol. Each of the agents added to the paste induced a change in viscosity. Adding substances supporting the maintenance of the construct or viability of cells and islets induces changes in the flowability of pastes that are insignificant to a point of being negligible. The paste from dECM constituted the basis for producing the primary bioink and for determination whether a particular bioink might be used for printing.

B. Methods of Bioink Solidification

Cross-Linking of Printouts Using Cross-Linking Agents

The table below presents the differences in the composition of cross-linking agents used in the primary bioink [Table 6].

TABLE 6

Various cross-linking agents used in the primary bioink.

| | | | GelMa/HAMA | | |
|---|---|---|---|---|---|
| Cross-linking agent | GelMa | HAMA | GelMa | HAMA | LAP |
| Concentration [% (w/v)] | 1.464-7.320 | 0.146-1.098 | 0.0732-5.490 | 0.0732-0.8235 | 0.03-0.17 |

Cross-linkability tests of the systems as above have been conducted using light with a wavelength in the range of 365 to 405 nm with a positive outcome [Table 7].

TABLE 7

% of damaged DNA by exposure to light of 365 and 405 nm wavelength

| | % of damaged DNA by exposure to light of 365 nm wavelength | | | % of damaged DNA by exposure to light of 405 nm wavelength | | |
|---|---|---|---|---|---|---|
| Exposure time (sec) | pancreatic islets | alpha cells of pancreatic islets | beta cells of pancreatic islets | pancreatic islets | alpha cells of pancreatic islets | beta cells of pancreatic islets |
| 0 sec | | 1.0% | 1.0% | | 4.0% | 4.0% |
| 10 sec | 12.0% | 2.0% | 1.5% | 2.0% | 2.5% | 1.5% |
| 30 sec | 14.0% | | | 5.5% | | |
| 60 sec | 45.0% | 5.0% | 1.5% | 2.0% | 3.5% | 2.0% |
| 90 sec | 18.0% | | | 9.5% | | |
| 120 sec | 19.0% | 6.0% | 2.0% | 3.5% | 16.0% | 5.5% |
| 180 sec | 20.0% | | | 5.0% | | |
| 300 sec | 50.0% | 7.5% | 2.0% | 6.0% | 9.5% | 3.0% |

The analysis of cross-linking results after the process or during the bioprinting process showed that both the use of 365 nm and 405 nm wavelength light achieved the intended effect, i.e. the change of hydrogel form from liquid to solid. However, since the bioink contains cells and microorganisms, only visible light may be used. Therefore, the most preferable method of cross-linking is to use light with a wavelength of 405 nm.

Adding supplementary chemical substances to the dECM paste resulted in smoothed topography of the filament surface. Moreover, an increase in the aeration of the bioink was identified when adding GelMa and HAMA, with this effect being the most potent with HAMA.

Thermal Gelation

Figure 3:
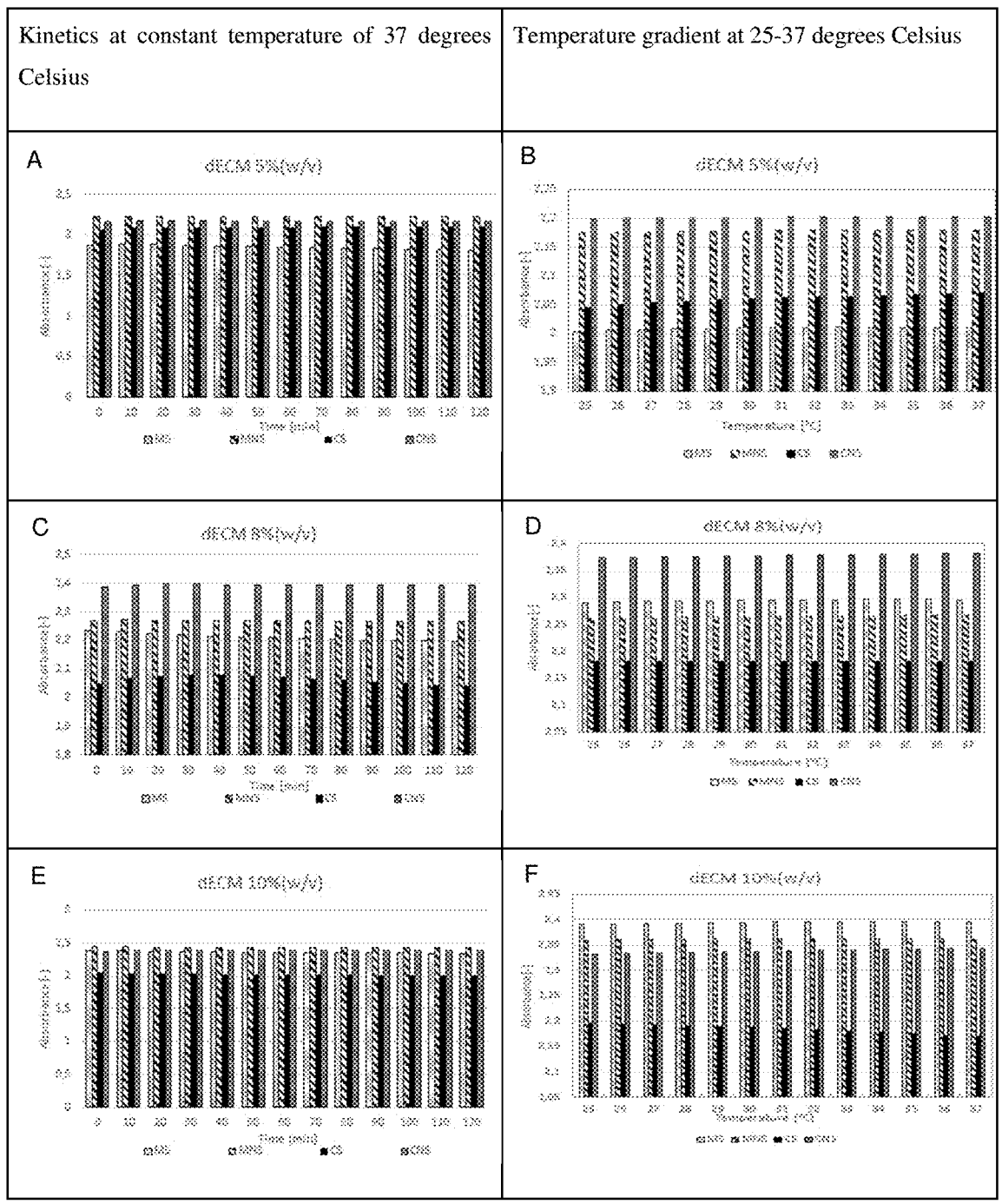
FIG. 3. Analysis of kinetics for 5% (w/v) dECM solutions (A, B), 8% (w/v) dECM solutions (C, D) and 10% (w/v) dECM solutions (E, F) at predetermined temperature.

The intensity of gelation process was tested using the identification of solution turbidity using specialised equipment over a wide range of temperatures and exposure time to the effect thereof. FIG. 3 shows examples of results from the dECM solution cross-linking test. For 5% (w/v) a slight increase in absorbance was observed for all the systems tested produced by temperature increase within the range of 25-37° C. The use of ground and sterile powder reduced the turbidity of the dECM solution. In case of higher dECM(r) concentrations (8 and 10% (w/v)) for cut powder solutions, the same sterilization correlation was obtained, whereas it was the opposite for ground powder. Both 8 and 10% (w/v) dECM(r) slightly increased their turbidity with the temperature increase. 10% dECM(r) exhibited relatively high turbidity and was stable in the tested temperature range Based on the kinetics of gelation at a constant temperature of 37° C., no significant changes in turbidity were observed when increasing the time of exposure to the temperature of 37° C. dECM(r) from ground sterile powder has the lowest absorbance value, while the cut non-sterile powder solution has the highest turbidity for all dECM(r) concentrations.

C. Bioink Component Permeability as Exemplified by Glucose Diffusion

With the increase of the so-called driving force, i.e. glucose concentration, the time of delay and reaching the state of equilibrium decreases, with the corresponding increase in diffusivity. The data presented in Table 8 show that the diffusivity of the membranes obtained with the primary bioink was comparable to those obtained with 4% (w/v) alginate (Alg4).

TABLE 8

Diffusivity of the membranes of the primary bioink supplemented with different additives. 4% alginate was added for comparison.

| | Glucose [mM] | | | | | |
|---|---|---|---|---|---|---|
| | 2.78 | | | 12.00 | | |
| parameter | t delay [min] | t plateau [min] | D [cm$^2$/s] | t delay [min] | t plateau [min] | D [cm$^2$/s] |
| Alg4 | 110.0 | 175.0 | 0.26 | 10.0 | 35.0 | 1.62 |
| HAMA | 77.5 | 122.5 | 0.36 | 10.0 | 55.0 | 1.85 |
| GelMa | 170.0 | 195.0 | 0.16 | 20.0 | 28.0 | 2.78 |
| HAMA/GelMa | 85.0 | 145.0 | 0.34 | 7.5 | 45.0 | 0.87 |

D. Absorbance

Figure 4:
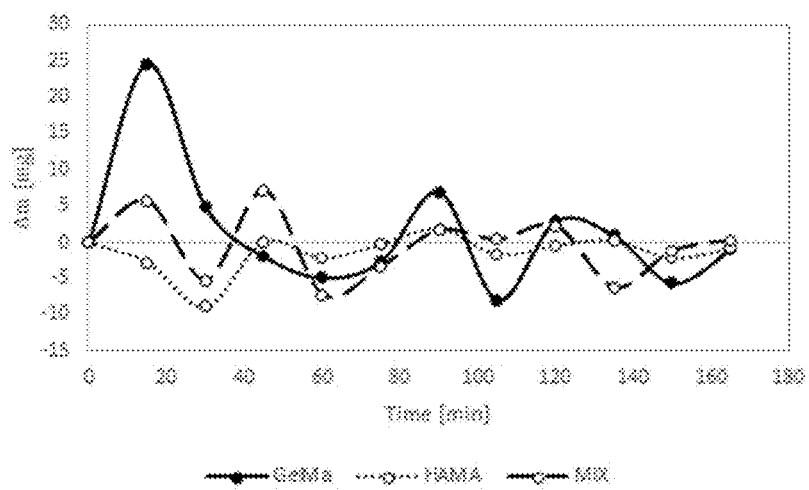
FIG. 4. Absorbency analysis of printed lobules: GelMa, HAMA, Mix.
Figure 5:
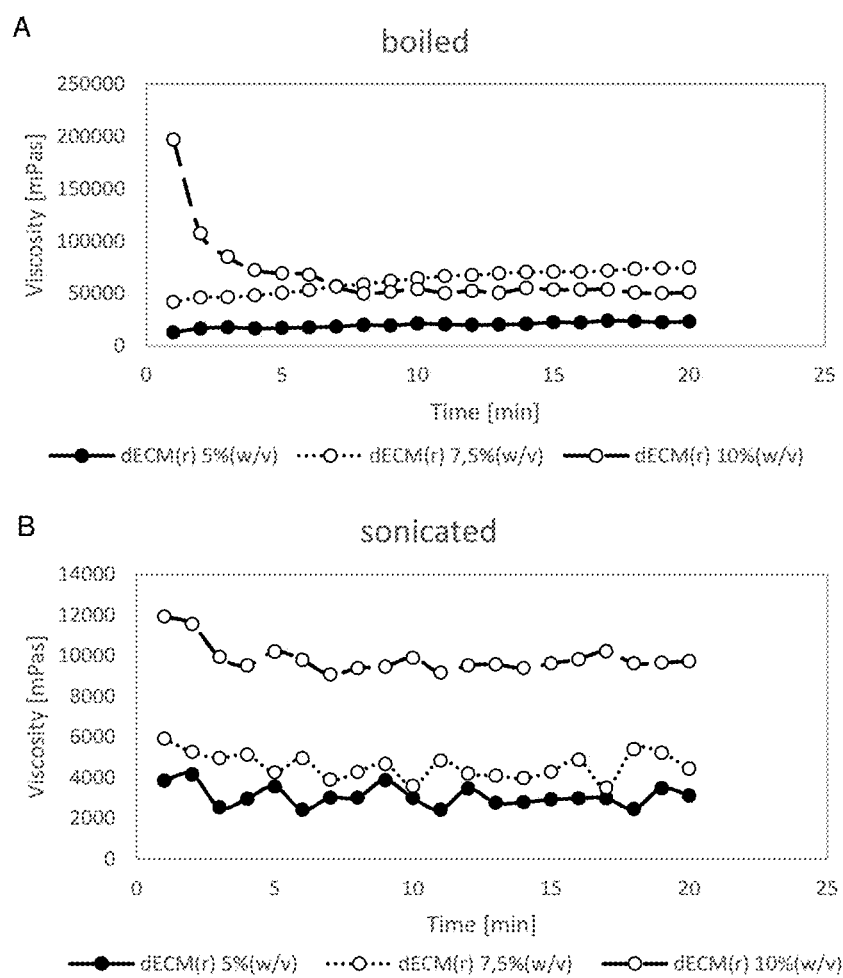
FIG. 5. Viscosities of A) boiled and B) sonicated dECM (r).

In order to evaluate the usability of the bioink obtained, absorbency analysis of printed lobules was carried out using a specially prepared buffer imitating the internal condition of the body. For the first 15 minutes, a slight increase in the weight of the printed construct was observed, followed by the decrease and stabilization thereof at a specific level. In the next step, changes in weight over time of the printed lobule were observed in order to study the phenomenon of degradation in the SBF buffer environment [FIG. 4].

Embodiment 4: Characteristics of Vascular Bioink

A. Rheology

Boiled dECM(r) has a much higher viscosity value than the sonicated one. However, due to proper stability of the vascular bioink after sonication, this method was determined to be more preferable for the printing of the vessel duct.

B. Gelation

An increase in temperature in the range 25 to 37° C. and exposure time to the temperature of 37° C. produces a slight decrease in boiled and sonicated dECM concentration.

TABLE 9

The effect of temperature on the concentration of
dECM used for the production of the vascular bioink

| | Absorbance of boiled dECM | | | Absorbance of sonicated dECM | | |
|---|---|---|---|---|---|---|
| T [° C.] | 5%(w/v) | 7.5%(w/v) | 10%(w/v) | 5%(w/v) | 7.5%(w/v) | 10%(w/v) |
| 25.4 | 2.248 | 2.401 | 2.236 | 2.514 | 3.028 | 3.030 |
| 26 | 2.247 | 2.401 | 2.234 | 2.513 | 3.027 | 3.028 |
| 27 | 2.247 | 2.401 | 2.230 | 2.513 | 3.028 | 3.031 |
| 28 | 2.247 | 2.400 | 2.225 | 2.514 | 3.027 | 3.029 |
| 29 | 2.246 | 2.400 | 2.221 | 2.513 | 3.031 | 3.029 |
| 30 | 2.246 | 2.399 | 2.222 | 2.514 | 3.030 | 3.030 |
| 31 | 2.245 | 2.399 | 2.220 | 2.514 | 3.029 | 3.030 |
| 32 | 2.244 | 2.399 | 2.212 | 2.514 | 3.029 | 3.030 |
| 33 | 2.244 | 2.398 | 2.210 | 2.514 | 3.029 | 3.028 |
| 34 | 2.243 | 2.398 | 2.209 | 2.514 | 3.033 | 3.029 |
| 35 | 2.242 | 2.397 | 2.208 | 2.514 | 3.031 | 3.027 |
| 36 | 2.242 | 2.396 | 2.209 | 2.513 | 3.030 | 3.028 |
| 37 | 2.241 | 2.393 | 2.209 | 2.513 | 3.032 | 3.028 |

TABLE 10

The effect of exposure time on the temperature of of 37° C. on
the concentration of dECM used for the production of the vascular bioink

| | Absorbance of boiled dECM | | | Absorbance of sonicated dECM | | |
|---|---|---|---|---|---|---|
| t [min] | 5%(w/v) | 7.5%(w/v) | 10%(w/v) | 5%(w/v) | 7.5%(w/v) | 10%(w/v) |
| 0 | 2.267 | 2.446 | 2.251 | 2.750 | 2.684 | 2.762 |
| 10 | 2.276 | 2.439 | 2.239 | 2.748 | 2.691 | 2.768 |
| 20 | 2.272 | 2.428 | 2.251 | 2.740 | 2.691 | 2.764 |
| 30 | 2.269 | 2.416 | 2.243 | 2.730 | 2.690 | 2.759 |
| 40 | 2.270 | 2.412 | 2.240 | 2.721 | 2.690 | 2.757 |
| 50 | 2.275 | 2.412 | 2.238 | 2.714 | 2.686 | 2.754 |
| 60 | 2.279 | 2.412 | 2.230 | 2.707 | 2.685 | 2.751 |
| 70 | 2.274 | 2.413 | 2.228 | 2.703 | 2.684 | 2.749 |
| 80 | 2.277 | 2.415 | 2.227 | 2.698 | 2.683 | 2.746 |
| 90 | 2.273 | 2.416 | 2.220 | 2.694 | 2.681 | 2.745 |
| 100 | 2.271 | 2.416 | 2.216 | 2.690 | 2.680 | 2.742 |
| 110 | 2.271 | 2.417 | 2.219 | 2.686 | 2.678 | 2.741 |
| 120 | 2.270 | 2.417 | 2.213 | 2.684 | 2.676 | 2.740 |

Embodiment 5: Effect of the Pressure Used During Bioprinting on the Viability of Cells and Microorgans Viability tests were performed on fibroblasts (cell lines 3T3-L1 and HFF-1) and pancreatic islets. For this purpose, pancreatic cells/islets were subjected to pressure in the range from 15 kPa to 100 kPa using a needle with a diameter of 0.2 and 0.6 mm. The results of the tests conducted showed that shear forces induced during 3D bioprinting using extrusion method produce significant changes in cell and microorgan viability.

TABLE 11

The percentage of living and dead 3T3-L1 cells
after applying predetermined pressures.

| | control | 15 kPa | 25 kPa | 30 kPa | 50 kPa | 75 kPa | 100 kPa |
|---|---|---|---|---|---|---|---|
| | Needle 0.6 mm | | | | | | |
| | 99% | 100% | 99% | 98% | 98% | 97% | 98% |
| p | — | 0.0817 | 1 | 0.1771 | 0.4368 | 0.067 | 0.1102 |
| | Needle 0.2 mm | | | | | | |
| | 97% | 97% | 95% | 94% | 87% | 89% | 97% |
| p | — | 0.0352 | 0.0247 | 0.0001 | 0 | <0.00001 | <0.00001 |

TABLE 12

The percentage of living and dead HFF-1 cells after applying predetermined pressures.

| | control | 15 kPa | 25 kPa | 30 kPa | 50 kPa | 75 kPa | 100 kPa |
|---|---|---|---|---|---|---|---|
| Needle 0.6 mm | | | | | | | |
| | 87% | 91% | 89% | 83% | 91% | 84% | 86% |
| p | — | 0.1947 | 0.6025 | 0.2606 | 0.1987 | 0.3478 | 0.6158 |
| Needle 0.2 mm | | | | | | | |
| | 87% | 74% | 74% | 79% | 82% | 78% | 80% |
| p | — | 0.0001 | 0 | 0.0061 | 0.0463 | 0.0018 | 0.0114 |

TABLE 13

The viability of pancreatic islets subjected to a particular pressure using a 0.6 mm needle. For pancreatic islets, it is preferable not to use a smaller needle diameter, as the diameter of pancreatic islets varies between 50 and 500 μm.

| | control | 15 kPa | 25 kPa | 30 kPa | 50 kPa | 75 kPa | 100 kPa |
|---|---|---|---|---|---|---|---|
| Porcine pancreatic islets - needle 0.6 mm | | | | | | | |
| | 100% | 78% | 92% | 71% | 64% | 86% | 75% |
| P | — | 0.22 | | 0.83 | 0.042 | 0.019 | 0.037 |
| Rat pancreatic islets - needle 0.2 mm | | | | | | | |
| | 86% | 95% | — | 56% | 66% | 35% | 22% |
| P | — | 1 | — | 0.001 | 0.019 | 0.002 | 0.0001 |

In order to obtain a viable and functional biological three-dimensional structure, the pressure and diameter of the needle needed to be matching the particular cell type. However, pressures of no more than 30 kPa were preferably applied.

Embodiment 5: Printability

Figure 6:
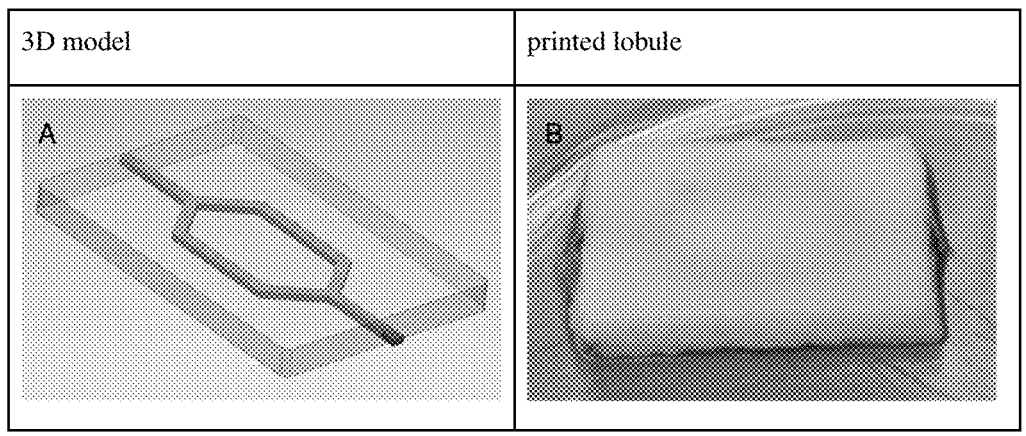
FIG. 6. 3D model of A) a vascularized lobule and B) a photo of the printed construct.
Figure 7:
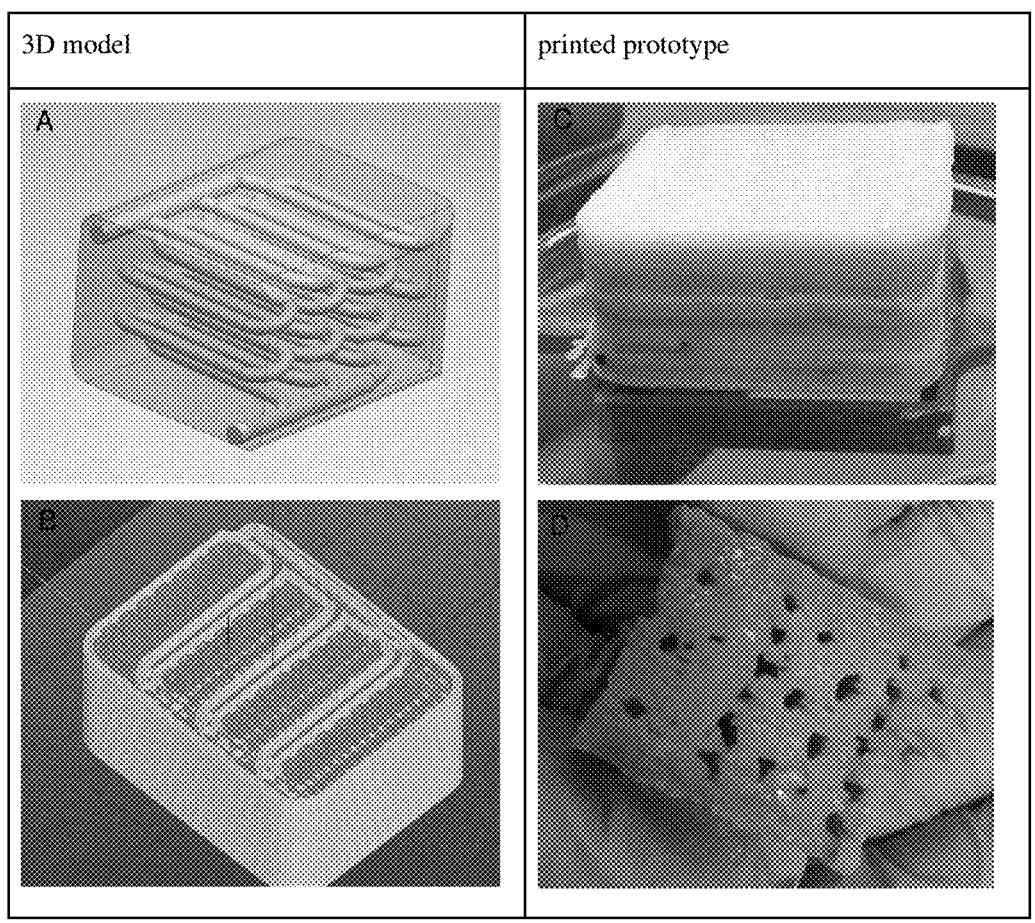
FIG. 7. Visualisation of the vascular system of the 3D model (A, B) and the prototype (C, D) of the pancreas.

Printouts using primary bioink were made using the following parameters: pressure: 4-100 kPa, printing speed: 5-40 mm/s, temperature: printhead—10-37° C.; printbed—4-37° C., needle diameter: 100 nm-1 mm Printouts using vascular bioink were made using the following parameters: pressure: 5-100 kPa, printing speed: 5-40 mm/s, temperature: printhead—10-37° C.; printbed—4-37° C., needle diameter: 100 nm-1 mm Lobule It took approx. 3 minutes to print a pancreatic lobule supplied with a vessel. FIG. 6 shows a 3D model of a vascularised lobule and a picture of the printed construct. SEM was used to identify the morphology of the lateral surface and cross-section of the printed lobule. A loose arrangement of bioink filaments was observed that was behind the substantial porosity of the lobule. Also, based on a cross-section analysis, the stratification of the three-dimensional porous structure supplied with patent ducts imitating vessels was identified.

Vascularised Three-Dimensional Structure

It took approximately 30 minutes to print a prototype of a bionic pancreas supplied with a network of patent ducts. As in the case of the lobule, a loose arrangement of bioink filaments in the highly porous structure of the printed construct supplied with a network of patent ducts was observed.

The printed vascular system was evaluated using nuclear magnetic resonance imaging. The 3D reconstructions made show patent ducts with no the tendency to collapse or dissect.

Embodiment 5: Cytotoxicity of the Printed Lobule

An MTT assay on a fibroblast line (3T3) was performed in order to assess cytotoxicity of the primary bioink. The result is presented as % of control at maximum extract concentration [Table 14]. Exposure time to the extract was 24 h and cells of density $1 \times 10^5$/mL were plated. Both assays showed no cytotoxicity to the cell line tested.

TABLE 14

Results of the MTT assay for cytotoxicity of the primary bioink. Tests conducted on the line of fibroblasts 3T3.

| MTT | Material | 3 D bioprinting form (max. concentration of the extract (100%)) |
|---|---|---|
| Extraction time (day) | 3T3 | % control |
| 1 | % control | 106.59 |
| | SD (%) | 7.72 |
| 7 | % control | 121.74 |
| | SD (%) | 9.29 |
| 14 | % control | 117.17 |
| | SD (%) | 10.18 |
| Positive control | % control | 7.37 |
| | SD (%) | 9.49 |

Embodiment 6: Effect of the Individual Bioink Components on the Functionality and Viability of Pancreatic Islets/Cells In order to assess the effect of the individual components of the primary bioink on the vitality and functionality of pancreatic islets, a glucose stimulation test was performed.

Glycerol

Figure 8:
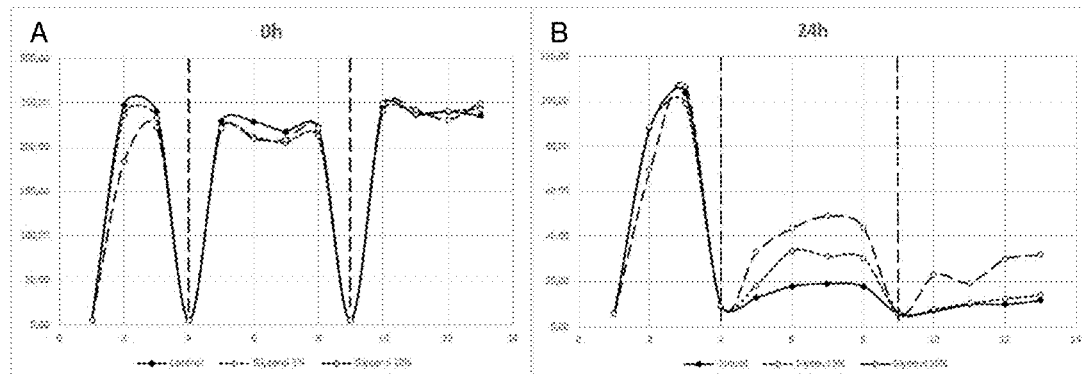
FIG. 8. The effect of glycerol on the functionality of pancreatic islets at A) the beginning of the experiment and B) after 24 h incubation.

Due to its properties, adding 5% (w/v) and 10% (w/v) glycerol to bioink improved the printability of the primary bioink. In order to assess its effect on pancreatic islet functionality, glycerol was added to culture medium at 5% or 10% concentration and the islets were incubated therein for 24 h [FIG. 8]. In both cases, the functionality of pancreatic islets is by far superior compared to pancreatic islets in the culture medium alone.

Commercially Available Protein Supplements

Figure 9:
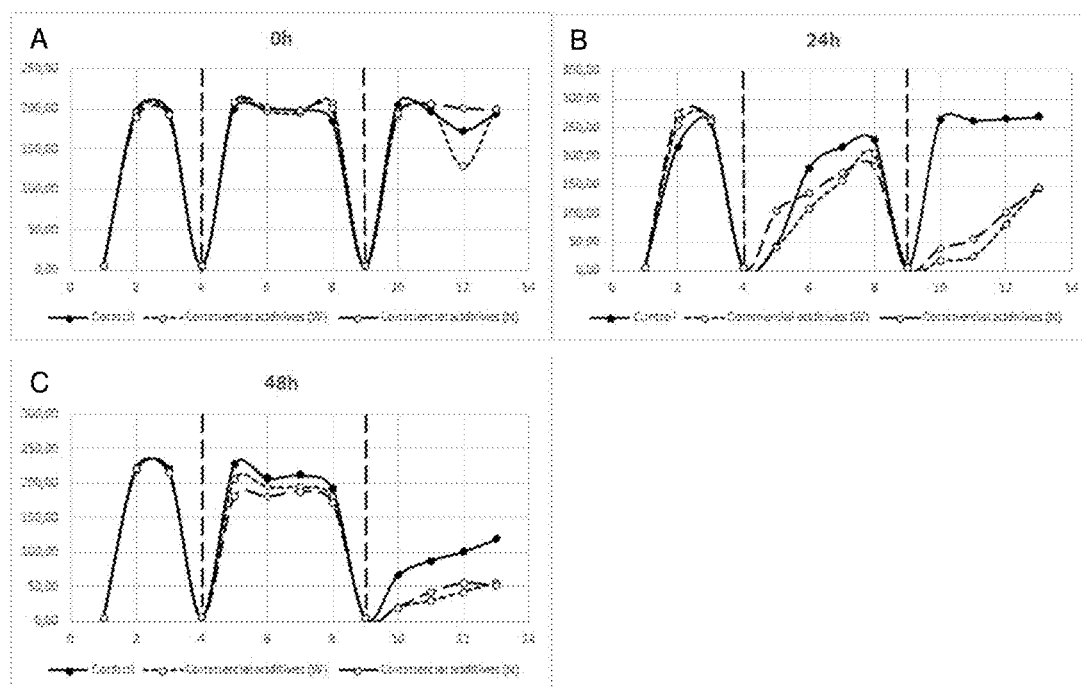
FIG. 9. The effect of commercial additives on the functionality and viability of pancreatic islets at A) the beginning of the experiment, B) after 24 h incubation and C) after 48 h incubation.

The effect was tested of adding extracellular matrix proteins on the functionality and viability of pancreatic islets. For this purpose, a solution consisting of 0.007 mg/mL hyaluronic acid, 0.041 mg/mL collagen I, 0.122 mg/mL collagen IV and 0.084 mg/mL laminin was prepared, which was added to the culture medium. The experiment was carried out with two types of hyaluronic acid: high molecular weight or low molecular weight, which were added to the culture medium and the islets were incubated therein for 48 h [FIG. 9]. In both the high (H) and low (L) molecular weight hyaluronic acid variants, pancreatic islets were functional at a level comparable to that of islets untreated with any supplements.

GelMA

Figure 10:
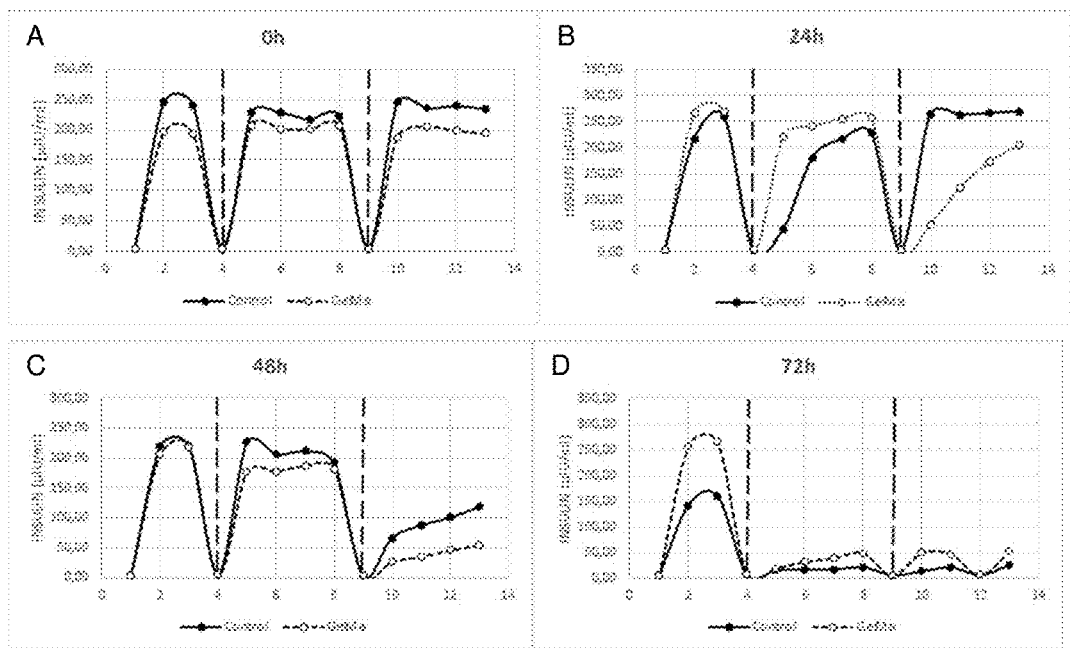
FIG. 10. The effect of adding methacrylated gelatin on the viability of pancreatic islets at A) the beginning of the experiment, B) after 24 h incubation, C) after 48 h incubation and D) after 48 h incubation.

It was tested how the viability of islets may be affected by methacrylated gelatin which, as a component of the bioink, is to ensure proper cross-linking of the print. For this purpose, 7.8% v/v GelMa was added to the culture medium and the islets were incubated therein for 72 h [FIG. 10]. The islets grown in the medium with GelMa added secreted similar or greater amounts of insulin depending on the time of measurement, which indicated a favourable effect of this compound at a given concentration on the viability of the islets.

HAMA

Figure 11:
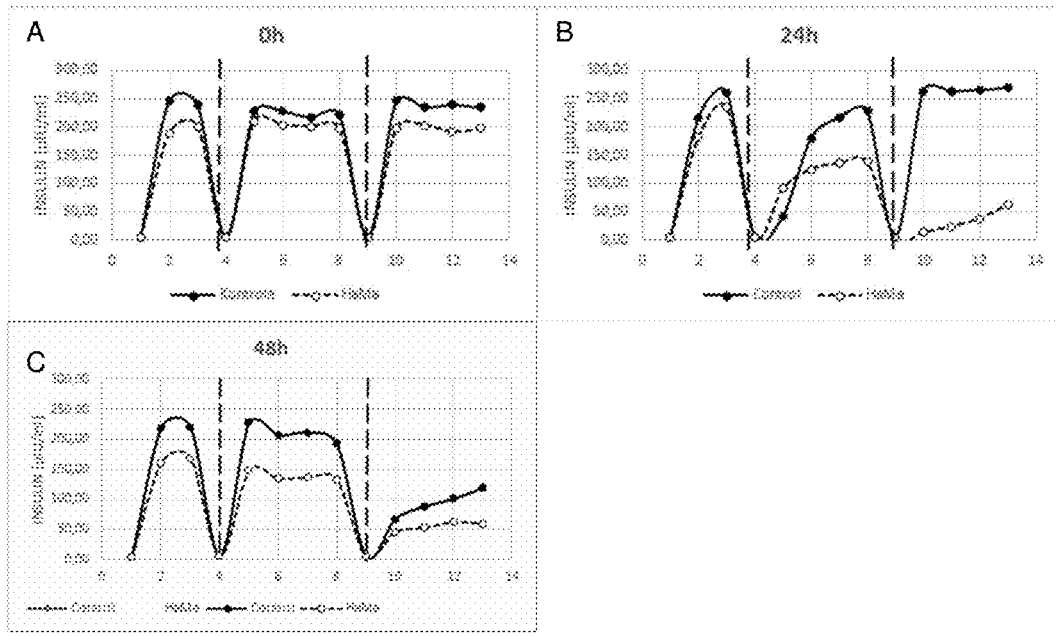
FIG. 11. The effect of adding methacrylated hyaluronic acid on the viability of pancreatic islets at A) the beginning of the experiment, B) after 24 h incubation and C) after 48 h incubation.

It was tested how the viability of islets may be affected by methacrylated hyaluronic acid, which, as a component of the bioink, is to ensure proper cross-linking of the print. For this purpose, 0.78% v/v HAMA was added to the culture medium and the islets were incubated therein for 48 h [FIG. 11]. The islets grown in the medium with HAMA secreted lower amounts of insulin than control islets, which may indicate an adverse effect of the compound in the tested concentration on the viability of the islets.

GelMA and HAMA

Figure 12:
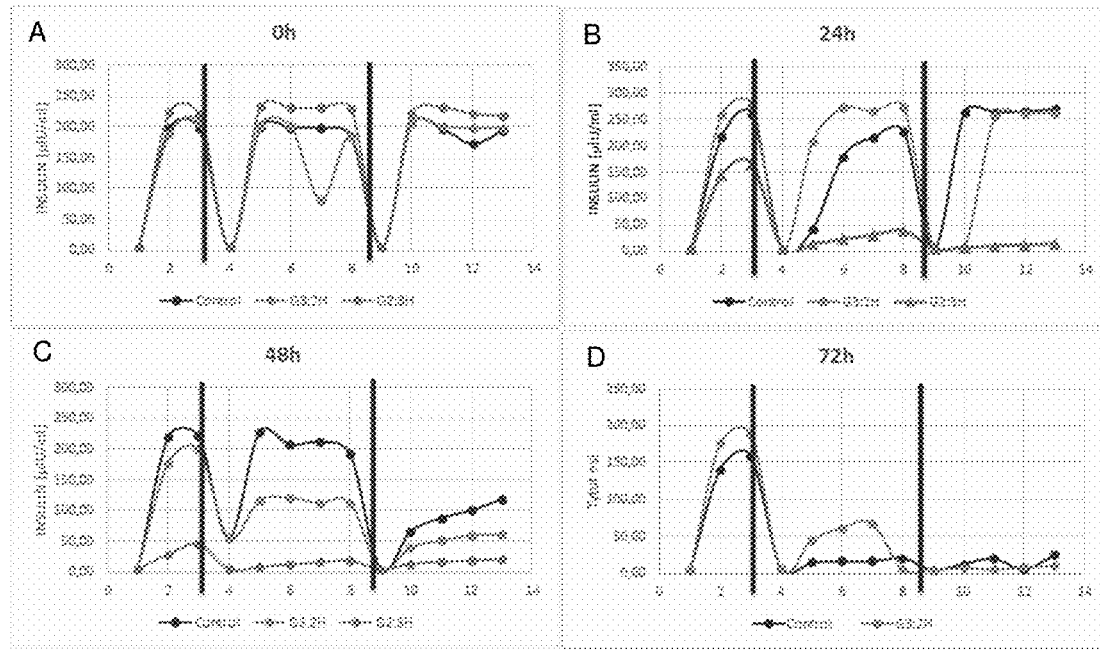
FIG. 12. The effect of the addition of the mixture of GelMa and HAMA in varying proportions on the viability of pancreatic islets at A) the beginning of the experiment, B) after 24 h incubation, C) after 48 h incubation and D) after 48 h incubation.

It was tested how the viability of islets may be affected by a mixture of methacrylated gelatin and methacrylated hyaluronic acid, which, as a component of the bioink, is to ensure proper cross-linking of the print. For this purpose, 4.68% v/v GelMa and 0.312% v/v HAMA (G3:2H) or 3.12% v/v GelMa and 0.468% v/v HAMA (G2:3H) were added to the culture medium and the islets were incubated therein for 72 h [FIG. 12]. The islets grown in the medium with the addition of the mixture in the G3:2H ratio secreted higher or lower amounts of insulin compared to the control islets, depending on the time point of measurement. This variant of the mixture seemed to have a favourable effect on the viability of the islets. The islets grown in the medium with the addition of the mixture in the ratio G2:3H secreted significantly less insulin than control islets, which indicated an adverse effect of the mixture of GelMa and HAMA at the given concentrations on the viability of the islets.

ECM Powder

Figure 13:
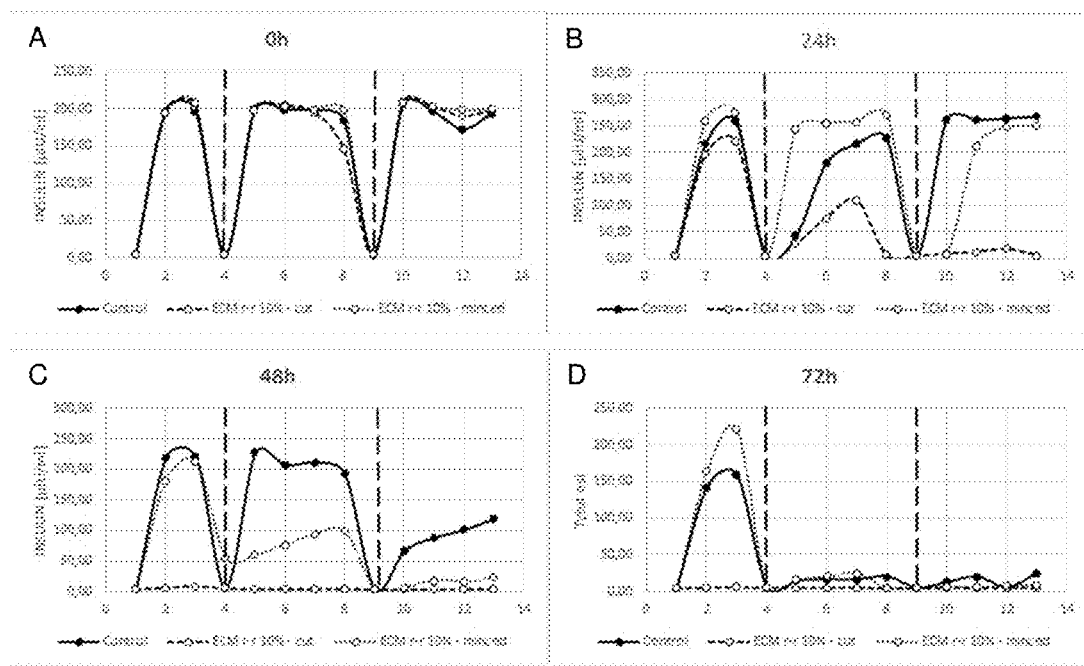
FIG. 13. The effect of adding cut or ground ECM powder on the viability of pancreatic islets at A) the beginning of the experiment, B) after 24 h incubation, C) after 48 h incubation and D) after 48 h incubation.

It was tested how the ECM obtained by way of decellularization could affect the viability of the islets. For this purpose, 3.33% v/v cut or ground ECM during decellularization was added to the culture medium and the islets were incubated therein for 72 h [FIG. 13]. The islets grown in the medium with the addition of ground ECM had a favourable effect on insulin secretion by the islets over 24 h. The medium with cut ECM added significantly reduced insulin secretion, which might indicate an adverse effect on islet viability.

Embodiment 7: Viability of Pancreatic Islets Following Bioprinting

Three bioinks were selected to assess the viability of pancreatic islets following 3D bioprinting: methacrylated gelatin, methacrylated hyaluronic acid, a mixture of methacrylated gelatin and methacrylated hyaluronic acid.

Figure 14:
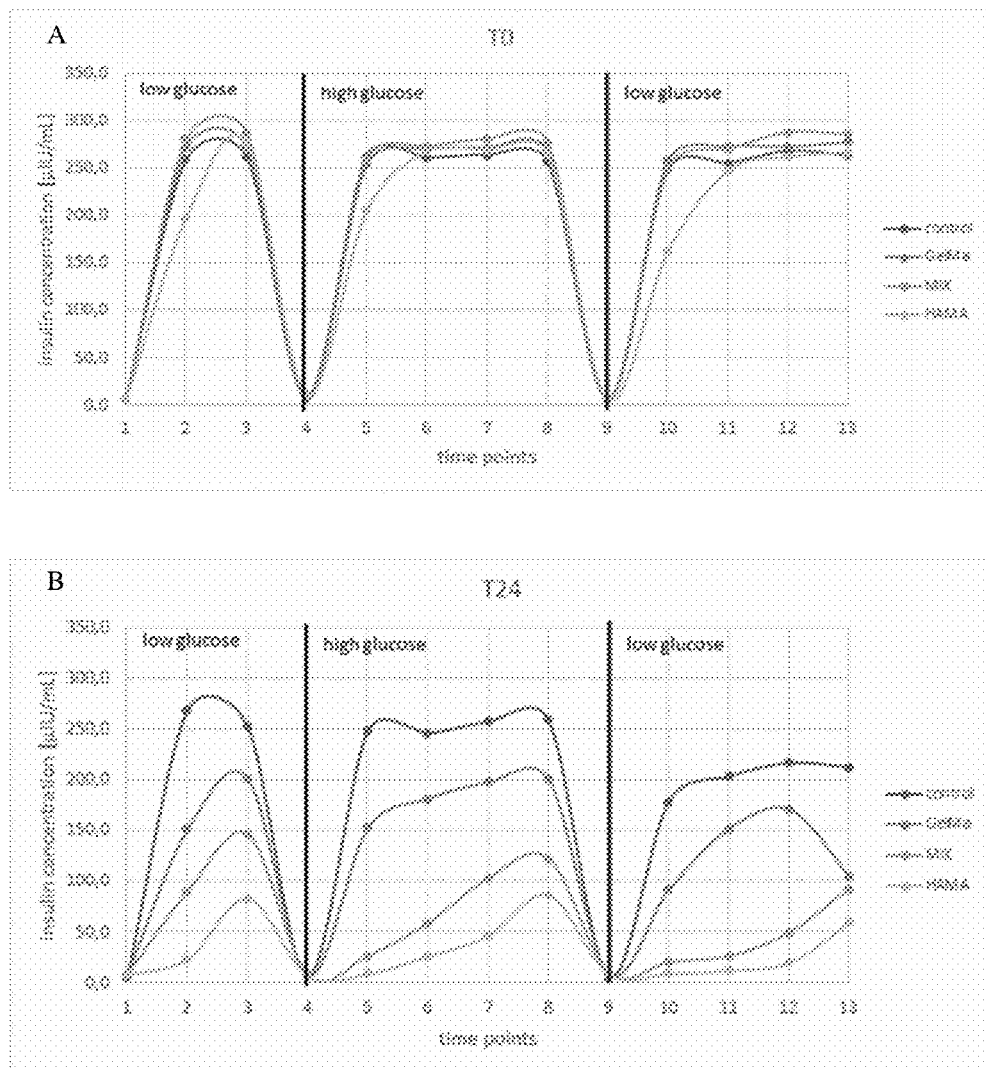
FIG. 14. The effect of the addition of GelMa and HAMA to the primary bioink on the viability of pancreatic islets after printing at A) the beginning of the experiment, B) after 24 h incubation.

For this purpose, 7.8% v/v GelMa or 0.78% v/v HAMA or a mixture of 4.68% v/v GelMa and 0.312% v/v HAMA (MIX) were added to the primary bioink. After printing, the lobules with islets were incubated in culture medium for 24 h [FIG. 14].

The islets in the lobule printed with the primary bioink, which contained an addition of GelMa, showed the highest level of insulin produced after the printing process, thus indicating a favourable effect of this component on the viability and functionality of pancreatic islets. Both the addition of HAMA and the mixture of GelMa and HAMA to the bioink induced a slight decrease in the levels of insulin produced by the islets compared to the control islets grown in the medium (that were not 3D bioprinted). Although the results for the bioink with the addition of GelMa alone showed the highest activity of the islets to the given glucose concentration, the structures printed were the least stable and they were the fastest to disintegrate in the culture medium. Therefore, the best solution was to use a mix of methacrylated gelatin and methacrylated hyaluronic acid for the bioprinting process. This combination allowed for preserving viable and functional pancreatic islets while maintaining proper bioprinting parameters and the stability of the printed model.

Figure 15:
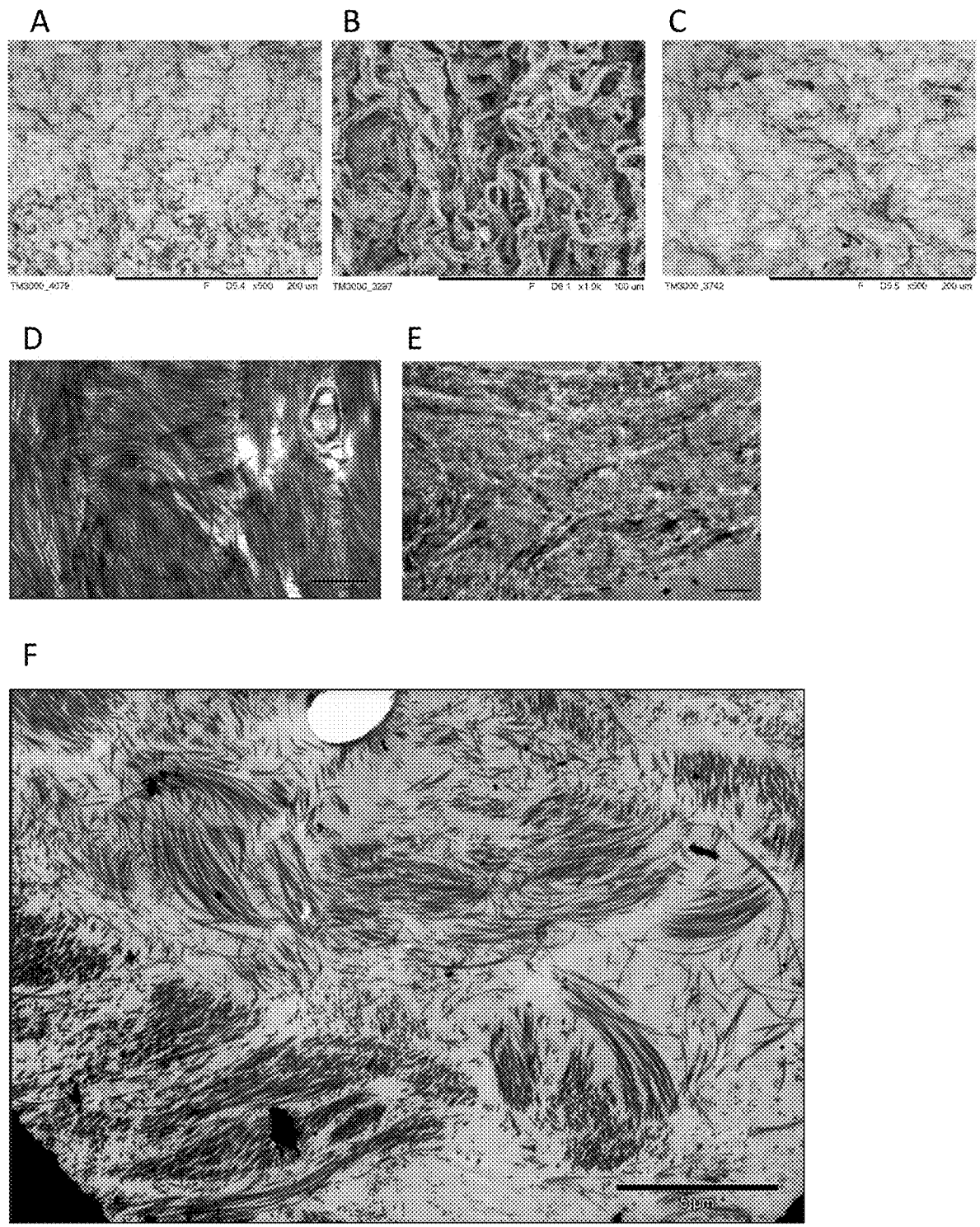
FIG. 15. Visualization from under an electron microscope presenting protein structure at individual stages of preparation of the dECM in order to use it as a raw material for bioprinting.

Embodiment 8: Confirmation of the Preserved Quaternary Structure of dECM in the Primary Bioink In order to visualize and confirm the preservation of the quaternary structure of ECM in the printed construct comprising the primary bioink, a visualization using electron microscopy of protein structures at individual stages of preparation of the dECM (in order to use it in bioprinting) was performed (FIG. 15). Printed constructs (E and F) comprising primary bioink exhibited collagen quaternary structure with visible collagen fibres.

The invention claimed is:
1. A detergent-free decellularized extracellular matrix (dECM) preparation method comprising the following steps:
   mechanical fragmentation by mechanical extrusion of an organ of animal origin selected from pancreas, liver, kidneys, heart, skin, lungs, large intestine, small intestine, blood arteries and veins, adipose tissue and placenta, wherein the organ is separate from the body of the animal;
   incubation of the fragmented organ in a buffered detergent solution comprising 1×PBS, whereby the buffered detergent solution comprises 0.5%-1.5% octoxynol-9, wherein the detergent solution is supplemented with an antimicrobial agent comprising streptomycin at a concentration of 0.01% (w/v), and the incubation is performed at a temperature below room temperature for at least 72 h with agitation, wherein the fragmented organ is transferred to a fresh detergent solution every 4 to 12 hours;
   incubation of the fragmented organ in a first buffered washing solution comprising 1×PBS, whereby the first buffered washing solution comprises an antimicrobial agent comprising streptomycin at a concentration of 0.01% (w/v), for at least 72 h at a temperature below room temperature with agitation, wherein the fragmented organ is transferred to a fresh washing solution every 4 to 12 hours;
   incubation of the fragmented organ in a deoxyribonuclease solution comprising DNAse at a concentration of 0.0001 to 0.0003% (w/v), for at least 8 hours at a temperature suitable for the DNAse performance;
   incubation of the fragmented organ in a second buffered washing solution comprising 1×PBS, whereby the second buffered washing solution comprises an antimicrobial agent comprising streptomycin at a concentration of 0.01% (w/v), for at least 72 h at a temperature below room temperature with agitation, wherein the fragmented organ is transferred to a fresh washing solution every 4 to 12 hours;
   freezing of the fragmented organ and crushing the frozen fragmented organ into fragments;
   freeze-drying of the frozen fragmented organ;
   optional final drying for 5 to 15 minutes at 0.0010 mbar (0.1 Pa) and −76° C.;

grinding the crushed and dried product into 25-500 pm dECM powder; and optional sterilization of the product by radiation and/or ethylene oxide.

2. The method according to claim 1, wherein the grinding step is followed by a step of checking the amount of octoxynol-9 in dECM powder, wherein before dECM powder is checked for the presence of octoxynol-9, it is treated with collagenase at a concentration of 43.9583 PZ/g dECM.

3. The method according to claim 1, wherein the grinding step is followed by the following steps:
dissolving of the dECM powder in hydrochloric acid solution supplemented with 0-10 mg/ml of pepsin;
mixing for 48-72 h at room temperature; neutralizing on ice using 0.1 M sodium base and PBS solution.

4. A method of preparation of a primary bioink comprising the following steps:
preparation of a paste comprising a) 5-50% (w/v) of the dECM powder obtained by the method defined in claim 1, and b) 1-10% (w/v) of a dECM solution obtained by dissolving the dECM powder obtained by the method defined in claim 1 in hydrochloric acid solution supplemented with 0-10 mg/ml of pepsin, mixing for 48-72 h at room temperature, and neutralizing on ice using 0.1 M sodium base and PBS solution;
incubation of the paste at a temperature of 7-10° C. for at least 24 hours;
addition of 1.46-7.32% (w/v) methacrylated gelatin, 0.15-1.10% (w/v) methacrylated hyaluronic acid and 5 to 10% (w/v) glycerol, and 0.03-0.17% (w/v) lithium phenyl-2,4,6-trimethylbenzoylphosphinate, followed by gentle mixing.

5. A primary bioink comprising a dECM paste and 1.46-7.32% (w/v) methacrylated gelatin, 0.15-1.10% (w/v) methacrylated hyaluronic acid and 5 to 10% (w/v) glycerol, and 0.03-0.17% (w/v) lithium phenyl-2,4,6-trimethylbenzoylphosphinate, wherein the dECM paste comprises a) 5-50% (w/v) of the dECM powder obtained by the method defined in claim 1, and b) 1-10% (w/v) of a dECM solution obtained by dissolving the dECM powder obtained by the method defined in claim 1 in hydrochloric acid solution supplemented with 0-10 mg/ml of pepsin, mixing for 48-72 h at room temperature, and neutralizing on ice using 0.1 M sodium base and PBS solution; and wherein the viscosity of the primary bioink is at least 5 Pas, measured in a cone-plate system, at a constant shear rate of 21/s and a temperature of 37° C.

6. The primary bioink according to claim 5, comprising at least one additive selected from: hyaluronic acid at a concentration of 0.001 to 0.100 mg/ml of the primary bioink, laminin at a concentration of 0.005 to 0.100 mg/ml of the primary bioink, collagen I at a concentration of 0.001 to 0.100 mg/ml of the primary bioink, collagen IV at a concentration of 0.005 to 0.175 mg/mL of the primary bioink, fibronectin at a concentration of 3 to 300 µg/mL, human fibrinogen at a concentration of 10 to 100 mg/ml of the primary bioink, aprotinin at a concentration of 1 to 2 EPU/mL of the primary bioink, polysorbate at a concentration of 0.05 to 2 mg/ml of the primary bioink, human thrombin at a concentration of 5 to 55 mg/ml of the primary bioink, calcium chloride at a concentration of 20 to 60 mM/mL of the primary bioink, vitamin A at a concentration of 1 nM-500 µM, vitamin B1 at a concentration of 50-100 µM, vitamin B3 at a concentration of 1 to 10 µM, vitamin B12 at a concentration of 10 to 100 mg/ml of the primary bioink, vitamin D3 at a concentration of 0.1 to 10 nM, VEGF at a concentration of 10 to 30 ng/ml of the primary bioink, FGF at a concentration of 10 to 20 ng/ml of the primary bioink, TGF-β at a concentration of 1 to 10 ng/ml of the primary bioink, interleukin (IL)-8 at a concentration of 0 to 100 ng/mL of the primary bioink, and IL-17A at a concentration of 20 to 50 ng/ml of the primary bioink.

7. The primary bioink according to claim 5, comprising one or more animal- or human-derived additives selected from endothelial cells at a density of $0.1\text{-}10\times10^5$/mL of the primary bioink, primary microvascular endothelial cells at a concentration of 0.1 to $10\times10^5$/mL of the primary bioink, animal- or human-derived α cells at a concentration of 3 to $9\times10^6$/mL of the bioink, animal- or human-derived β cells at a concentration of 1.1 to $3.4\times10^7$/mL of the bioink, and animal- or human-derived pancreatic islets in the amount of 20,000 iEq/mL of the primary bioink.

8. A method of preparation of a vascular bioink comprising the steps of:
a) optional preparation of a solution of microbiological gelatin supplemented with CMC comprising preparation of a 1-2% (w/v) solution of microbiological gelatin in a buffer solution comprising PBS, by suspending microbiological gelatin in the buffer solution with agitation at a temperature between 5° and 65° C., addition of a 2-5% (v/v) carboxymethyl cellulose (CMC) aqueous solution to obtain a final concentration of 0.2-1% (v/v) of CMC in the vascular bioink and cooling the solution to a temperature equal or below 40° C.;
b) preparation of a 5-10% (w/v) dECM solution by addition of the dECM powder obtained by the method defined in claim 1, sterilized by radiation, to (i) the solution of microbiological gelatin supplemented with CMC obtained in step a) or (ii) a buffer solution or (iii) a solution of cell medium with gentle agitation;
c) sonication of the obtained solution at a temperature not exceeding 37° C. for 0.5-2.0 hours;
d) optional addition of at least one animal- or human-derived additive selected from: fibronectin at a concentration of 3 to 300 µg/mL, VEGF at a concentration of 10 to 30 ng/ml, FGF at a concentration of 10 to 20 ng/ml, PGE2 at a concentration between 100 and 300 nM, endothelial cells at a density between 0.1 and $10\times10^7$ cells/mL of the bioink, and fibroblasts at a density of between 0.1 and $10\times10^6$ cells/mL of the bioink.

9. A method of preparation of a vascular bioink comprising the steps of:
a) optional preparation of a solution of microbiological gelatin supplemented with CMC comprising preparation of a 1-2% (w/v) solution of microbiological gelatin in a buffer solution comprising PBS, by suspending microbiological gelatin in the buffer solution with agitation at a temperature between 5° and 65° C., addition of a 2-5% (v/v) carboxymethyl cellulose (CMC) aqueous solution to obtain a final concentration of 0.2-1% (v/v) of CMC in the vascular bioink and cooling the solution to a temperature equal or below 40° C.;
b) preparation of a 5-10% (w/v) dECM solution by addition of dECM powder obtained by the method defined in claim 1, sterilized by radiation, to (i) the solution of microbiological gelatin supplemented with CMC obtained in step a) or (ii) a buffer solution or (iii) a solution of cell medium with gentle agitation;
c) boiling the mixture at 100° C. for 15-30 minutes;
d) optional addition of at least one animal- or human-derived additive selected from: fibronectin at a concentration of 3 to 300 µg/mL, VEGF at a concentration of 10 to 30 ng/ml, FGF at a concentration of 10 to 20 ng/ml, PGE2 at a concentration between 100 and 300 nM, endothelial cells at a density between 0.1 and $10 \times 10^7$ cells/mL of the bioink, and fibroblasts at a density of between 0.1 and $10 \times 10^6$ cells/mL of the bioink.

10. A vascular bioink comprising sonicated or boiled dECM solution obtained by the method defined in claim 3 at a concentration of 2-10% (w/v), supplemented with microbiological gelatin at a concentration of 1 to 5% (w/v) and/or CMC at a concentration of 0.2 to 2% (v/v).

11. The vascular bioink according to claim 10, comprising at least one animal- or human-derived additive selected from: fibronectin at a concentration of 3 to 300 µg/mL, VEGF at a concentration of 10 to 30 ng/ml, FGF at a concentration of 10 to 20 ng/mL, PGE2 at a concentration between 100 and 300 nM, endothelial cells at a density between 0.1 and $10 \times 10^7$ cells/mL of the bioink, and fibroblasts at a density of between 0.1 and $10 \times 10^6$ cells/mL of the bioink.

12. A three-dimensional structure comprising at least three adjacent bioink layers, wherein a layer of a vascular bioink is arranged between two layers of a primary bioink;

wherein the vascular bioink is obtained by a) dissolving the dECM powder obtained by the method of claim 1 in hydrochloric acid solution supplemented with 0-10 mg/ml of pepsin, mixing for 48-72 h at room temperature, and neutralizing on ice using 0.1 M sodium base and PBS solution to obtain a dECM solution; and b) sonicating or boiling the dECM solution at a concentration of 2-10% (w/v), supplemented with microbiological gelatin at a concentration of 1 to 5% (w/v) and/or CMC at a concentration of 0.2 to 2% (v/v); and the primary bioink comprises a dECM paste and 1.46-7.32% (w/v) methacrylated gelatin, 0.15-1.10% (w/v) methacrylated hyaluronic acid and 5 to 10% (w/v) glycerol, and 0.03-0.17% (w/v) lithium phenyl-2,4,6-trimethylbenzoylphosphinate, wherein the dECM paste comprises a) 5-50% (w/v) of the dECM powder obtained by the method of claim 1, and b) 1-10% (w/v) of a dECM solution obtained by dissolving the dECM powder obtained in claim 1 in hydrochloric acid solution supplemented with 0-10 mg/ml of pepsin, mixing for 48-72 h at room temperature, and neutralizing on ice using 0.1 M sodium base and PBS solution; and wherein the viscosity of the primary bioink is at least 5 Pa·s, measured in a cone-plate system, at a constant shear rate of 21/s and a temperature of 37° C.

13. A method of preparation of a three-dimensional structure, wherein a primary bioink and a vascular bioink are deposited layer by layer in a 3D-bioprinting process at a printing speed from 5 to 50 mm/s, pressure from 4 to 300 kPa and temperature from 4 to 37° C. and wherein during or after deposition the primary bioink is exposed to UV light and/or visible light of the wavelength from 365 to 405 nm for at least 5 seconds;

wherein the vascular bioink is obtained by a) dissolving the dECM powder obtained by the method of claim 1 in hydrochloric acid solution supplemented with 0-10 mg/ml of pepsin, mixing for 48-72 h at room temperature, and neutralizing on ice using 0.1 M sodium base and PBS solution to obtain a dECM solution; and b) sonicating or boiling the dECM solution at a concentration of 2-10% (w/v), supplemented with microbiological gelatin at a concentration of 1 to 5% (w/v) and/or CMC at a concentration of 0.2 to 2% (v/v); and the primary bioink comprises a dECM paste and 1.46-7.32% (w/v) methacrylated gelatin, 0.15-1.10% (w/v) methacrylated hyaluronic acid and 5 to 10% (w/v) glycerol, and 0.03-0.17% (w/v) lithium phenyl-2,4,6-trimethylbenzoylphosphinate, wherein the dECM paste comprises a) 5-50% (w/v) of the dECM powder obtained by the method of claim 1, and b) 1-10% (w/v) of a dECM solution obtained by dissolving the dECM powder obtained in claim 1 in hydrochloric acid solution supplemented with 0-10 mg/ml of pepsin, mixing for 48-72 h at room temperature, and neutralizing on ice using 0.1 M sodium base and PBS solution; and wherein the viscosity of the primary bioink is at least 5 Pa·s, measured in a cone-plate system, at a constant shear rate of 21/s and a temperature of 37° C.

* * * * *